(12) United States Patent
Sebastian et al.

(10) Patent No.: US 11,882,867 B2
(45) Date of Patent: *Jan. 30, 2024

(54) HEAT CONDUCTING SUBSTRATE FOR ELECTRICALLY HEATED AEROSOL DELIVERY DEVICE

(71) Applicant: RAI Strategic Holdings, Inc., Winston-Salem, NC (US)

(72) Inventors: Andries Sebastian, Clemmons, NC (US); Stephen Benson Sears, Siler City, NC (US); Billy Tyrone Conner, Clemmons, NC (US); Rajesh Sur, Winston-Salem, NC (US); S. Keith Cole, Advance, NC (US); Thaddeus Jackson, High Point, NC (US); Timothy Frederick Thomas, High Point, NC (US); Paul E. Braxton, Summerfield, NC (US); Curtis Foster Doe, Winston-Salem, NC (US); Vahid Hejazi, Winston-Salem, NC (US); Kathryn Lynn Wilberding, High Point, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 147 days.

This patent is subject to a terminal disclaimer.

(21) Appl. No.: 17/244,139

(22) Filed: Apr. 29, 2021

(65) Prior Publication Data

US 2021/0244070 A1    Aug. 12, 2021

Related U.S. Application Data

(63) Continuation of application No. 15/905,320, filed on Feb. 26, 2018, now Pat. No. 11,019,850.

(51) Int. Cl.
A24B 3/14    (2006.01)
A24B 13/02    (2006.01)
(Continued)

(52) U.S. Cl.
CPC ............... *A24B 3/14* (2013.01); *A24B 13/02* (2013.01); *A24D 1/002* (2013.01); *A24D 1/14* (2013.01);
(Continued)

(58) Field of Classification Search
CPC .............................. A24B 13/02; A24D 1/002
See application file for complete search history.

(56) References Cited

U.S. PATENT DOCUMENTS

| 1,514,682 A | 11/1924 | Wilson |
| 1,771,366 A | 7/1930 | Wyss et al. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report from the corresponding International Appl. No. PCT/IB2019/051503, dated Jul. 8, 2019.

*Primary Examiner* — Kelly M Gambetta
*Assistant Examiner* — Jennifer A Kessie
(74) *Attorney, Agent, or Firm* — WOMBLE BOND DICKINSON (US) LLP

(57) ABSTRACT

The present disclosure provides aerosol generating substrates and aerosol source members comprising aerosol generating substrates, as well as methods of manufacturing thereof. In an example implementation, an aerosol generating substrate may comprise a fibrous filler material, an aerosol forming material, and a plurality of heat conducting (Continued)

constituents, wherein the substrate is formed as a sheet, and wherein the heat conducting constituents are part of the sheet. The heat conducting constituents may be incorporated within the sheet, or may be formed on a surface of the sheet. In another example implementation, an aerosol source member may comprise a substrate portion formed of a collection of intermingled pieces cut from an aerosol substrate sheet. In addition, or alternatively, a substrate portion may be formed of a series of overlapping layers of an aerosol substrate sheet.

15 Claims, 11 Drawing Sheets

(51) Int. Cl.
  A24D 1/00  (2020.01)
  A24D 1/20  (2020.01)
  A24D 1/14  (2006.01)
  A24F 40/20  (2020.01)
  A24F 40/465  (2020.01)
  H05B 3/34  (2006.01)
  A61M 15/06  (2006.01)
  A61M 11/04  (2006.01)
(52) U.S. Cl.
  CPC ............. *A24D 1/20* (2020.01); *A61M 11/042* (2014.02); *A61M 15/06* (2013.01); *H05B 3/342* (2013.01); *A24F 40/20* (2020.01); *A24F 40/465* (2020.01)

(56) References Cited

U.S. PATENT DOCUMENTS

| | | |
|---|---|---|
| 2,057,353 A | 10/1936 | Whittemore, Jr. |
| 2,104,266 A | 1/1938 | McCormick |
| 3,200,819 A | 8/1965 | Gilbert |
| 3,479,561 A | 11/1969 | Janning |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,101,839 A | 4/1992 | Jakob et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,598,868 A | 2/1997 | Jakob et al. |
| 5,613,505 A | 3/1997 | Campbell et al. |
| 5,649,554 A | 7/1997 | Sprinkel et al. |
| 5,666,977 A | 9/1997 | Higgins et al. |
| 5,687,746 A | 11/1997 | Rose et al. |
| 5,697,385 A | 12/1997 | Seymour et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 9,078,473 B2 | 7/2015 | Worm et al. |
| 9,717,277 B2 | 8/2017 | Mironov |
| 9,788,571 B2 | 10/2017 | Conner et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0068543 A1 | 3/2007 | Chen |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Heibrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |

(56) References Cited

U.S. PATENT DOCUMENTS

| | | |
|---|---|---|
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2016/0037826 A1 | 2/2016 | Hearn et al. |
| 2016/0295921 A1 | 10/2016 | Mironov et al. |
| 2017/0055576 A1 | 3/2017 | Beeson et al. |
| 2017/0064996 A1 | 3/2017 | Mironov |
| 2017/0071250 A1 | 3/2017 | Mironov et al. |
| 2017/0079325 A1* | 3/2017 | Mironov .................. A24B 3/14 |
| 2017/0086508 A1 | 3/2017 | Mironov et al. |
| 2017/0119049 A1* | 5/2017 | Blandino ................ A24F 40/46 |
| 2017/0119054 A1 | 5/2017 | Zinovik |
| 2017/0164657 A1 | 6/2017 | Batista |
| 2017/0172208 A1 | 6/2017 | Mironov |
| 2019/0053535 A1* | 2/2019 | Apetrei Birza ........... A24F 7/00 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 994 000 | 3/2016 |
| EP | 3 145 338 | 3/2017 |
| EP | 3 145 341 | 3/2017 |
| EP | 3 145 346 | 3/2017 |
| EP | 3 266 323 A1 | 1/2018 |
| EP | 3 506 772 | 7/2019 |
| EP | 3 527 087 | 8/2019 |
| GB | 2469850 | 11/2010 |
| RU | 2 638 514 C2 | 12/2017 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2015/177247 | 11/2015 |
| WO | WO 2015/177255 | 11/2015 |
| WO | WO 2016/199066 | 12/2016 |
| WO | WO 2017/005705 | 1/2017 |
| WO | WO 2017/068091 | 4/2017 |
| WO | WO 2017/068092 | 4/2017 |
| WO | WO 2017/068093 | 4/2017 |
| WO | WO 2017/068094 | 4/2017 |
| WO | WO 2017/068096 | 4/2017 |
| WO | WO 2017/068098 | 4/2017 |
| WO | WO 2017/068099 | 4/2017 |
| WO | WO 2017/068100 | 4/2017 |
| WO | 2017/072147 A2 | 5/2017 |
| WO | WO 2017/085242 | 5/2017 |
| WO | WO 2017/153443 | 9/2017 |
| WO | WO 2017/178394 | 10/2017 |
| WO | WO 2018/041450 | 3/2018 |
| WO | WO 2018/048450 | 3/2018 |
| WO | WO 2018/096000 | 5/2018 |
| WO | WO 2019/030000 | 2/2019 |
| WO | WO 2019/030167 | 2/2019 |
| WO | WO 2019/030170 | 2/2019 |
| WO | WO 2019/030353 | 2/2019 |
| WO | WO 2019/030363 | 2/2019 |
| WO | WO 2019/030366 | 2/2019 |
| WO | WO 2019/197170 | 10/2019 |
| WO | WO 2019/219867 | 11/2019 |
| WO | WO 2020/174026 | 9/2020 |
| WO | WO 2020/174027 | 9/2020 |
| WO | WO 2020/174028 | 9/2020 |
| WO | WO 2020/174029 | 9/2020 |

* cited by examiner

HEAT CONDUCTING SUBSTRATE FOR ELECTRICALLY HEATED AEROSOL DELIVERY DEVICE

CROSS-REFERENCE TO RELATED APPLICATIONS

This application is a continuation application of U.S. patent application Ser. No. 15/905,320, filed on Feb. 26, 2018, which is incorporated herein in its entirety by reference.

FIELD OF THE DISCLOSURE

The present disclosure relates to aerosol delivery articles and uses thereof for yielding tobacco components or other materials in inhalable form. More particularly, the present disclosure relates to substrate materials and aerosol source members containing substrate materials for aerosol delivery devices and systems, such as smoking articles, that utilize electrically-generated heat to heat a tobacco or non-tobacco material, preferably without significant combustion, in order to provide an inhalable substance in the form of an aerosol for human consumption.

DESCRIPTION OF RELATED ART

Many smoking articles have been proposed through the years as improvements upon, or alternatives to, smoking products based upon combusting tobacco. Exemplary alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference in its entirety. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and PCT Pat. App. Pub. No. WO 2010/091593 to Hon, which are incorporated herein by reference in their entireties.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKERo by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™; IQOS™ by Philip Morris International; and GLO™ by British American Tobacco.

Articles that produce the taste and sensation of smoking by electrically heating tobacco, tobacco derived materials, or other plant derived materials have suffered from inconsistent performance characteristics. For example, some articles have suffered from inconsistent release of flavors or other inhalable materials. Accordingly, it can be desirable to provide a smoking article that can provide the sensations of cigarette, cigar, or pipe smoking, that does so without combusting the substrate material, that does so without the need of a combustion heat source, and that does so with increased performance characteristics.

BRIEF SUMMARY

In various implementations, the present disclosure provides an aerosol generating substrate for use in an aerosol source member. In one implementation, the substrate may comprise a fibrous filler material, an aerosol forming material, and a plurality of heat conducting constituents. The substrate may be formed as a sheet, and the heat conducting constituents may be part of the sheet. Some implementations further comprise a binder material. In some implementations, the heat conducting constituents may be incorporated within the sheet. In some implementations, the heat conducting constituents may be formed on a surface of the sheet. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the heat conducting constituents may be formed in a segmented pattern. In some implementations, the segmented pattern may be created using at least one of printing, laminating, stitching, and selective adhesion. In some implementations, the plurality of heat conducting constituents may comprise at least one of a metal mesh laminate and a metal fiber cloth laminate. In some implementations, the fibrous filler material may comprise at least one of a tobacco material and a tobacco-derived material. In some implementations, the fibrous filler material comprises a non-tobacco material. In some implementations, the segmented pattern may be created using a masking template.

Another implementation provides an aerosol source member for use with an aerosol delivery device that may comprise a substrate portion comprising a fibrous filler material, an aerosol forming material, and a plurality of heat conducting constituents. The substrate portion may be formed of a collection of intermingled pieces cut from an initial substrate sheet formed by the fibrous filler material, aerosol forming material, and plurality of heat conducting constituents, and the heat conducting constituents may be incorporated within the initial substrate sheet. In some implementations, the substrate portion may further comprise a binder material. In some implementations, the form of the heat conducting constituents in the initial substrate sheet may comprise at least one of a granular form, a powder form, a fiber form, a mesh form, and a fiber cloth form. In some implementations, the material of the heat conducting constituents in the initial substrate sheet may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material of the initial substrate sheet may comprise at least one of a tobacco material and a tobacco-derived material. In some implementations, the fibrous filler material of the initial substrate sheet may comprise a non-tobacco material.

Another implementation provides an aerosol source member for use with an aerosol delivery device that may comprise a substrate portion comprising a fibrous filler material, an aerosol forming material, and a plurality of heat conducting constituents. The substrate portion may be formed of a series of overlapping layers of an initial substrate sheet formed by the fibrous filler material, aerosol forming material, and plurality of heat conducting constituents, and the heat conducting constituents may be incorporated within the initial substrate sheet. In some implementations, the substrate portion may further comprise a binder material. In some implementations, the form of the heat conducting constituents in the initial substrate sheet may comprise at least one of a granular form, a powder form, a fiber form, a mesh form, and a fiber cloth form. In some implementations, the material of the heat conducting constituents in the initial substrate sheet may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material in the initial substrate sheet may comprise at least one of a tobacco material and a tobacco-derived material. In some implementations, the fibrous filler material in the initial substrate sheet may comprise a non-tobacco material.

Another implementation provides an aerosol source member for use with an aerosol delivery device that may comprise a wrap portion, and a substrate portion comprising a fibrous filler material, an aerosol forming material, and a plurality of heat conducting constituents. The substrate portion may be formed of a collection of intermingled pieces cut from an initial sheet formed by the fibrous filler material, aerosol forming material, and plurality of heat conducting constituents, the heat conducting constituents may be incorporated within the initial substrate sheet, the wrap portion may comprise an overwrap sheet configured to wrap around the substrate portion, and the overwrap sheet may include a plurality of heat conducting constituents. In some implementations, the substrate portion may further comprise a binder material. In some implementations, the form of the heat conducting constituents of the overwrap sheet may comprise at least one of a granular form, a powder form, a fiber form, a mesh form, and a fiber cloth form. In some implementations, the material of the heat conducting constituents of the overwrap sheet may comprise at least one of a metal material, a metal alloy material, a ceramic material, a carbon material, and a polymeric fiber material coated with a metal material. In some implementations, the plurality of heat conducting constituents of the substrate portion may comprise at least one of a metal mesh laminate and a metal fiber cloth laminate. In some implementations, the fibrous filler material in the initial substrate sheet may comprise a tobacco or tobacco-derived material. In some implementation, the fibrous filler material in the initial substrate sheet may comprise a non-tobacco material.

Another implementation provides an aerosol source member for use with an aerosol delivery device that may comprise a wrap portion, and a substrate portion comprising a fibrous filler material, an aerosol forming material, and a plurality of heat conducting constituents. The substrate portion may be formed of a series of overlapping layers of a sheet formed by the fibrous filler material, aerosol forming material, and plurality of heat conducting constituents, the heat conducting constituents may be incorporated within the sheet, the wrap portion may comprise an overwrap sheet configured to wrap around the substrate portion, and the overwrap sheet may include a plurality of heat conducting constituents. In some implementations, the substrate portion may further comprise a binder material. In some implementations, the form of the heat conducting constituents of the overwrap sheet may comprise at least one of a granular form, a powder form, a fiber form, a mesh form, and a fiber cloth form. In some implementation, the material of the heat conducting constituents of the overwrap sheet may comprise at least one of a metal material, a metal alloy material, a ceramic material, a carbon material, and a polymeric fiber material coated with a metal material. In some implementations, the plurality of heat conducting constituents of the substrate portion may comprise at least one of a metal mesh laminate or a metal fiber cloth laminate. In some implementations, the fibrous filler material in the initial substrate sheet may comprise at least one of a tobacco material and a tobacco-derived material. In some implementations, the fibrous filler material in the initial substrate sheet may comprise a non-tobacco material.

Another implementation provides an aerosol source member for use with an induction heated aerosol delivery device having a resonant transmitter. In one implementation, the aerosol source member may comprise a substrate portion comprising a fibrous filler material, an aerosol forming material, and a plurality of heat conducting constituents. The substrate portion may be formed of a collection of intermingled pieces cut from an initial substrate sheet formed by the fibrous filler material, aerosol forming material, and plurality of heat conducting constituents, the heat conducting constituents may be incorporated within the initial substrate sheet, and the plurality of heat conducting constituents may comprise a resonant receiver configured to exhibit an alternating current when exposed to an oscillating magnetic field from the resonant transmitter. In some implementations, the substrate portion may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material may comprise at least one of a tobacco material and a tobacco-derived material. In some implementations, the fibrous filler material may comprise a non-tobacco material.

Another implementation provides an aerosol source member for use with an induction heated aerosol delivery device having a resonant transmitter. In one implementation, the aerosol source member may comprise a substrate portion comprising a fibrous filler material, an aerosol forming material, and a plurality of heat conducting constituents. The substrate portion may be formed of a series of overlapping layers of an initial substrate sheet formed by the fibrous filler material, aerosol forming material, and plurality of heat conducting constituents, the heat conducting constituents may be incorporated within the initial substrate sheet, and the plurality of heat conducting constituents may comprise a resonant receiver configured to exhibit an alternating current when exposed to an oscillating magnetic field from the resonant transmitter. In some implementations, the substrate portion may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material in the initial substrate sheet may comprise at least one of a tobacco material or a tobacco-derived material. In some implementations, the fibrous filler material in the initial substrate sheet may comprise a non-tobacco material.

Another implementation provides an aerosol source member for use with an induction heated aerosol delivery device having a resonant transmitter. In one implementation, the aerosol source member may comprise a substrate portion comprising a fibrous filler material, an aerosol forming material, and a plurality of heat conducting constituents. The substrate portion may be formed of a collection of granules formed by an extruded and spheronized mixture of the fibrous filler material, aerosol forming material, and plurality of heat conducting constituents, and the plurality of heat conducting constituents may comprise a resonant receiver configured to exhibit an alternating current when exposed to an oscillating magnetic field from the resonant transmitter. In some implementations, the substrate portion may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material may comprise at least one of a tobacco material and a tobacco-derived material. In some implementations, the fibrous filler material may comprise a non-tobacco material.

Another implementation provides a method of manufacturing an aerosol generating substrate for use in an aerosol source member. In one implementation, the method may comprise providing a fibrous filler material, an aerosol forming material, and a plurality of heat conducting constituents, and forming a substrate sheet using the fibrous filler material, the aerosol forming material, and the plurality of heat conducting constituents. The heat conducting constituents may be part of the substrate sheet. Some implementations may further comprise providing a binder material, and the step of forming the substrate sheet may further comprise using the binder material. In some implementations, the heat conducting constituents may be incorporated within the substrate sheet. In some implementations, the heat conducting constituents may be formed on a surface of the substrate sheet. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the heat conducting constituents may be formed in a segmented pattern. In some implementations, the segmented pattern may be created using at least one of printing, laminating, stitching, and selective adhesion. In some implementations, the plurality of heat conducting constituents may comprise at least one of a metal mesh laminate and a metal fiber cloth laminate. In some implementations, the fibrous filler material may comprise at least one of a tobacco material and a tobacco-derived material. In some implementations, the fibrous filler material may comprise a non-tobacco material. In some implementations, the segmented pattern may be created using a masking template.

Another implementation provides a method of manufacturing an aerosol source member for use with an aerosol delivery device. In one implementation, the method may comprise forming an initial substrate sheet comprising a fibrous filler material, an aerosol forming material, and a plurality of heat conducting constituents, wherein the heat conducting constituents are incorporated within the initial substrate sheet, cutting the initial substrate sheet into a plurality of pieces, forming a collection of intermingled pieces from the plurality of pieces of the initial substrate sheet, and forming a substrate portion using the collection of intermingled pieces. In some implementations, the initial substrate sheet may further comprise a binder material. In some implementations, the form of the heat conducting constituents in the initial substrate sheet may comprise at least one of a granular form, a powder form, a fiber form, a mesh form, and a fiber cloth form. In some implementations, the material of the heat conducting constituents in the initial substrate sheet may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material of the initial substrate sheet may comprise at least one of a tobacco material and a tobacco-derived material. In some implementations, the fibrous filler material of the initial substrate sheet may comprise a non-tobacco material.

Another implementation provides a method of manufacturing an aerosol source member for use with an aerosol delivery device. In one implementation, the method may comprise forming an initial substrate sheet comprising a fibrous filler material, an aerosol forming material, and a plurality of heat conducting constituents, wherein the heat conducting constituents are incorporated within the initial substrate sheet, overlapping a plurality of layers of the initial substrate sheet, and forming a substrate portion using the overlapping layers. In some implementations, the initial substrate sheet may further comprise a binder material. In some implementations, the form of the heat conducting constituents in the initial substrate sheet may comprise at least one of a granular form, a powder form, a fiber form, a mesh form, and a fiber cloth form. In some implementations, the material of the heat conducting constituents in the initial substrate sheet may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material in the initial substrate sheet may comprise at least one of a tobacco material and a tobacco-derived material. In some implementations, the fibrous filler material in the initial substrate sheet may comprise a non-tobacco material.

Another implementation provides a method of forming an aerosol source member for use with an aerosol delivery device. In one implementation, the method may comprise forming an initial substrate sheet comprising a fibrous filler material, an aerosol forming material, and a plurality of heat conducting constituents, wherein the heat conducting constituents are incorporated within the initial substrate sheet, cutting the initial substrate sheet into a plurality of pieces, forming a collection of intermingled pieces from the plurality of pieces of the initial substrate sheet, forming a substrate portion using the collection of intermingled pieces, and forming a wrap portion. The wrap portion may comprise an overwrap sheet configured to wrap around the substrate portion, and the overwrap sheet may include a plurality of heat conducting constituents. In some implementations, the initial substrate sheet may further comprise a binder material. In some implementations, the form of the heat conducting constituents of the overwrap sheet may comprise at least one of a granular form, a powder form, a fiber form, a mesh form, and a fiber cloth form. In some implementations, the material of the heat conducting constituents of the overwrap sheet may comprise at least one of a metal material, a metal alloy material, a ceramic material, a carbon material, and a polymeric fiber material coated with a metal material. In some implementations, the plurality of heat conducting constituents of the substrate portion may comprise at least one of a metal mesh laminate and a metal fiber cloth laminate. In some implementations, the fibrous filler material in the initial substrate sheet may comprise at least one of a tobacco material and a tobacco-derived material. In some implementations, the fibrous filler material in the initial substrate sheet may comprise a non-tobacco material.

Another implementation provides a method of manufacturing an aerosol source member for use with an aerosol delivery device. In one implementation, the method may comprise forming an initial substrate sheet comprising a fibrous filler material, an aerosol forming material, and a plurality of heat conducting constituents, wherein the heat conducting constituents are incorporated within the initial substrate sheet, overlapping a plurality of layers of the initial substrate sheet, forming a substrate portion using the overlapping layers, and forming a wrap portion. The wrap portion may comprise an overwrap sheet configured to wrap around the substrate portion, and the overwrap sheet may include a plurality of heat conducting constituents. In some implementations, the initial substrate sheet may further comprise a binder material. In some implementations, the form of the heat conducting constituents of the overwrap sheet may comprise at least one of a granular form, a powder form, a fiber form, a mesh form, and a fiber cloth form. In some implementations, the material of the heat conducting constituents of the overwrap sheet may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material in the initial substrate sheet may comprise a tobacco or tobacco-derived material. In some implementations, the fibrous filler material in the initial substrate sheet may comprise a non-tobacco material.

Another implementation provides a method of manufacturing an aerosol source member for use with an induction heated aerosol delivery device having a resonant transmitter. In one implementation, the method may comprise forming an initial substrate sheet comprising a fibrous filler material, an aerosol forming material, and a plurality of heat conducting constituents, wherein the heat conducting constituents are incorporated within the initial substrate sheet, cutting the initial substrate sheet into a plurality of pieces, forming a collection of intermingled pieces from the plurality of pieces of the initial substrate sheet, and forming a substrate portion using the collection of intermingled pieces. The plurality of heat conducting constituents may comprise a resonant receiver configured to exhibit an alternating current when exposed to an oscillating magnetic field from the resonant transmitter. In some implementations, the initial substrate sheet may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material may comprise a tobacco or tobacco-derived material. In some implementations, the fibrous filler material may comprise a non-tobacco material. Another implementation provides a method of manufacturing an aerosol source member for use with an induction heated aerosol delivery device having a resonant transmitter. In one implementation, the method comprises forming an initial substrate sheet comprising a fibrous filler material, an aerosol forming material, and a plurality of heat conducting constituents, wherein the heat conducting constituents are incorporated within the initial substrate sheet, overlapping a plurality of layers of the initial substrate sheet, and forming a substrate portion using the overlapping layers. The plurality of heat conducting constituents may comprise a resonant receiver configured to exhibit an alternating current when exposed to an oscillating magnetic field from the resonant transmitter. In some implementations, the initial substrate sheet may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material in the initial substrate sheet may comprise a tobacco or tobacco-derived material. In some implementations, the fibrous filler material in the initial substrate sheet may comprise a non-tobacco material.

Another implementation provides a method of manufacturing an aerosol source member for use with an induction heated aerosol delivery device having a resonant transmitter. In one implementation, the method may comprise forming a mixture comprising a fibrous filler material, an aerosol forming material, and a plurality of heat conducting constituents, extruding and spheronizing the mixture into a plurality of granules, forming a collection of the granules; and forming substrate portion using the collection of granules. The plurality of heat conducting constituents may comprise a resonant receiver configured to exhibit an alternating current when exposed to an oscillating magnetic field from the resonant transmitter. In some implementations, the mixture may further comprise a binder material. In some implementations, the form of the heat conducting constituents may comprise at least one of a granular form, a powder form, a fiber form, a mesh form, and a fiber cloth form. In some implementations, the material of the heat conducting constituents may comprise at least one of a metal material, a metal alloy material, a ceramic material, a carbon material, and a polymeric fiber material coated with a metal material. In some implementations, the plurality of heat conducting constituents may comprise at least one of a metal mesh laminate and a metal fiber cloth laminate. In some implementations, the fibrous filler material may comprise a tobacco or tobacco-derived material. In some implementations, the fibrous filler material may comprise a non-tobacco material. These and other features, aspects, and advantages of the disclosure will be apparent from a reading of the following detailed description together with the accompanying drawings, which are briefly described below.

BRIEF DESCRIPTION OF THE FIGURES

Figure 1:
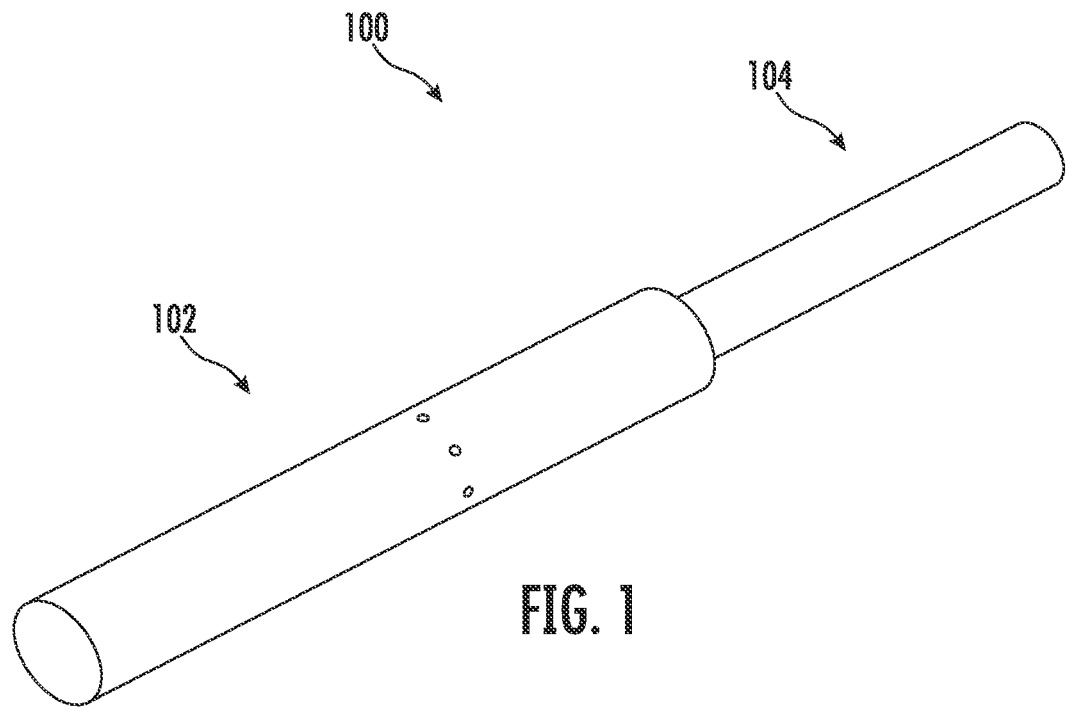
Figure 2:
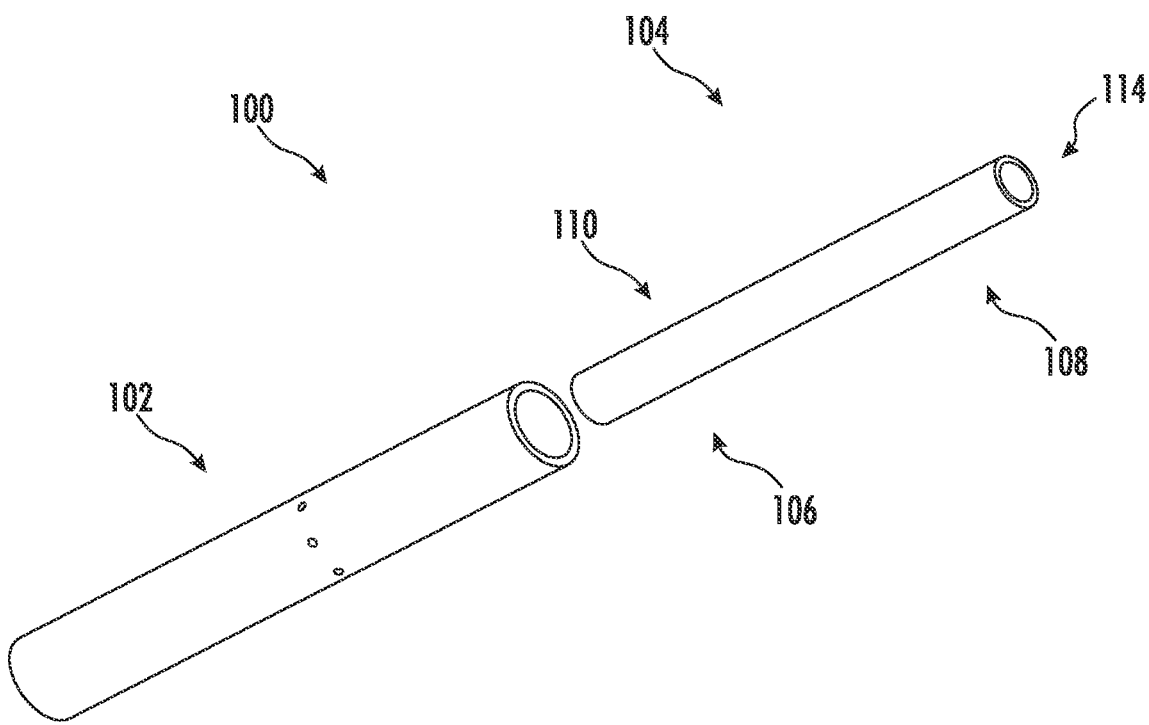
Figure 3:
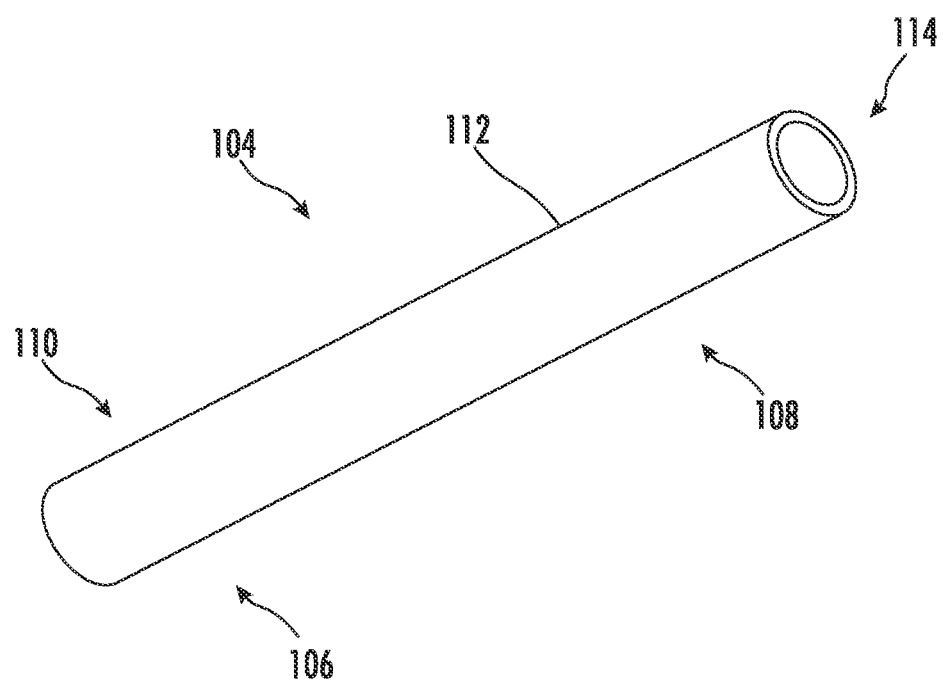
Figure 4:
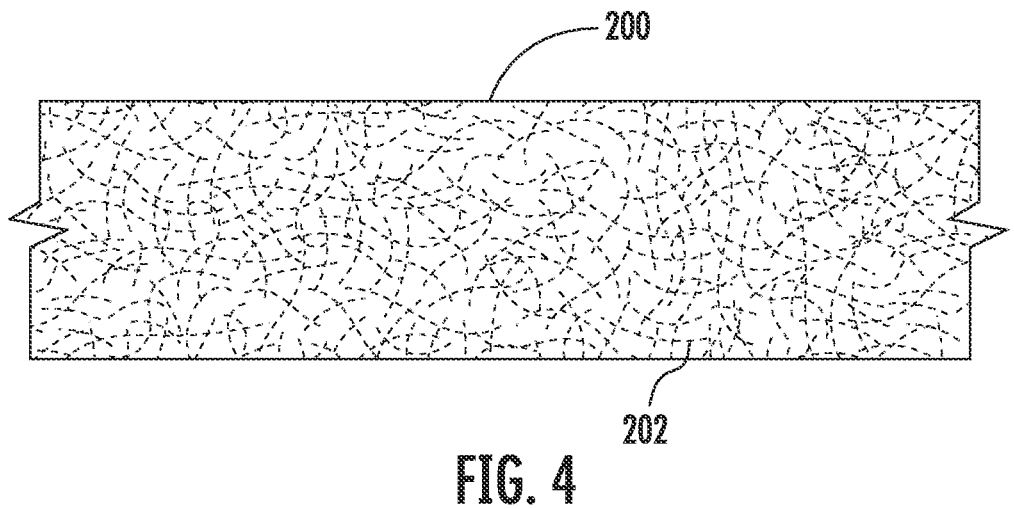
Figure 5:
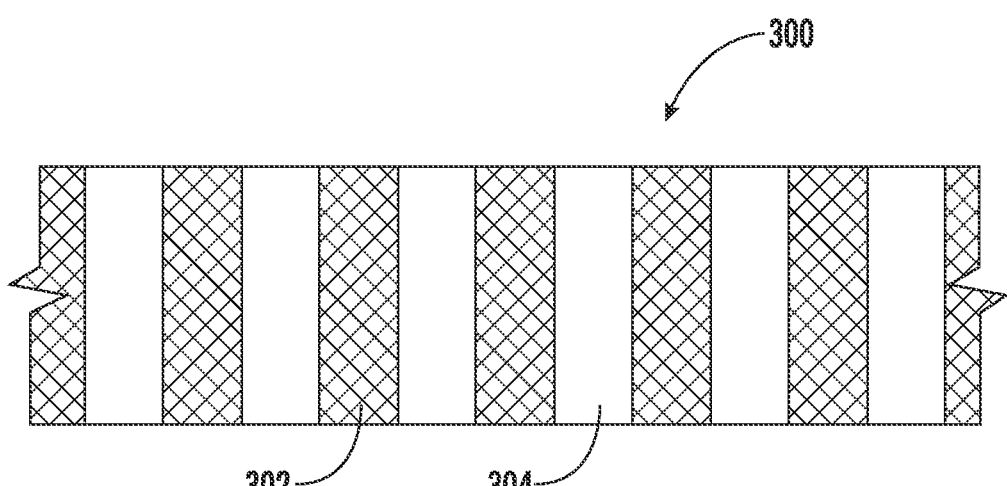
Figure 6:
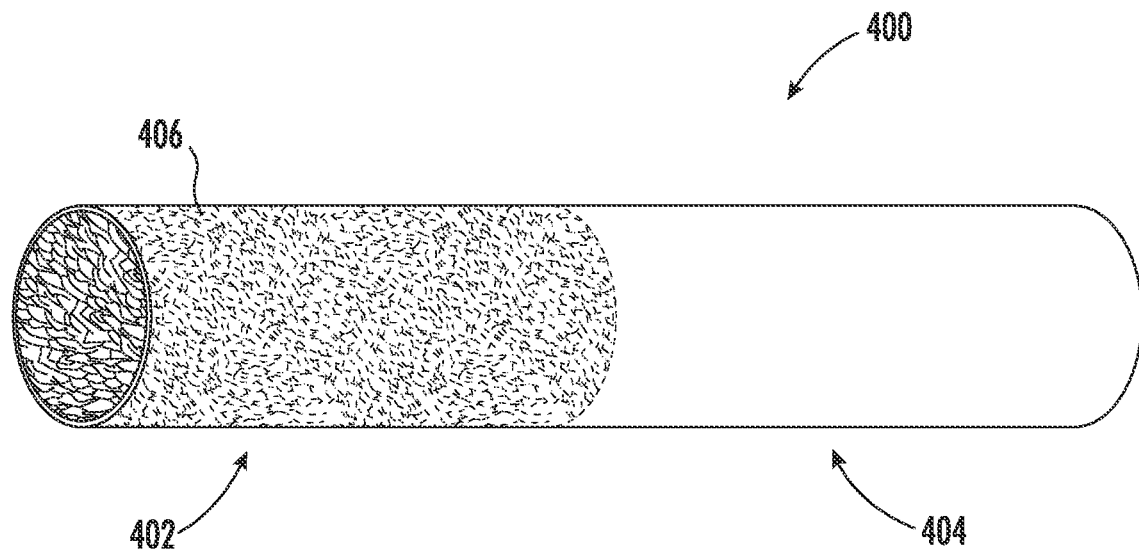
Figure 7:
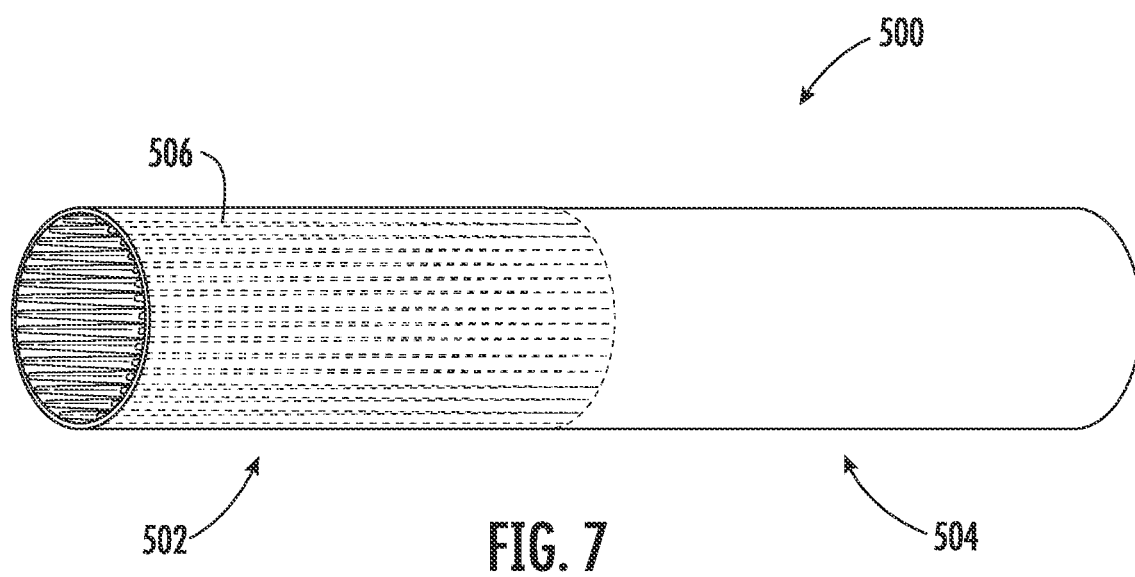
Figure 8:
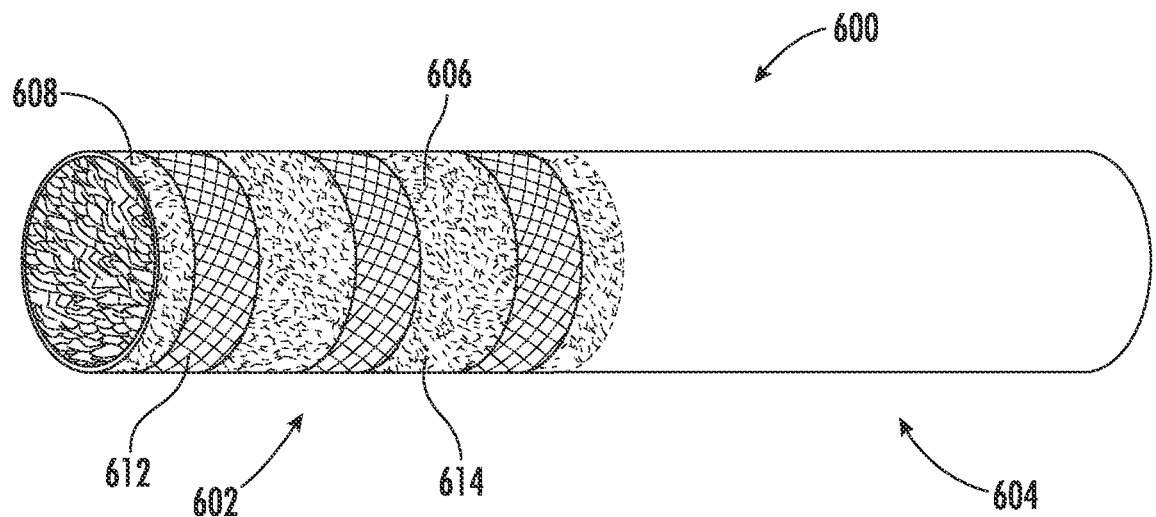
Figure 9:
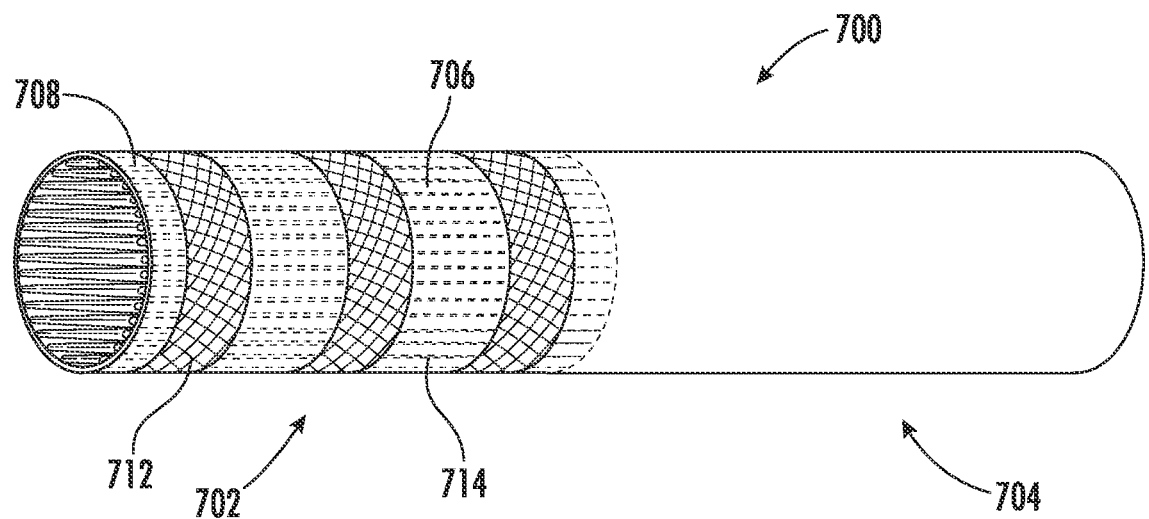
Figure 10:
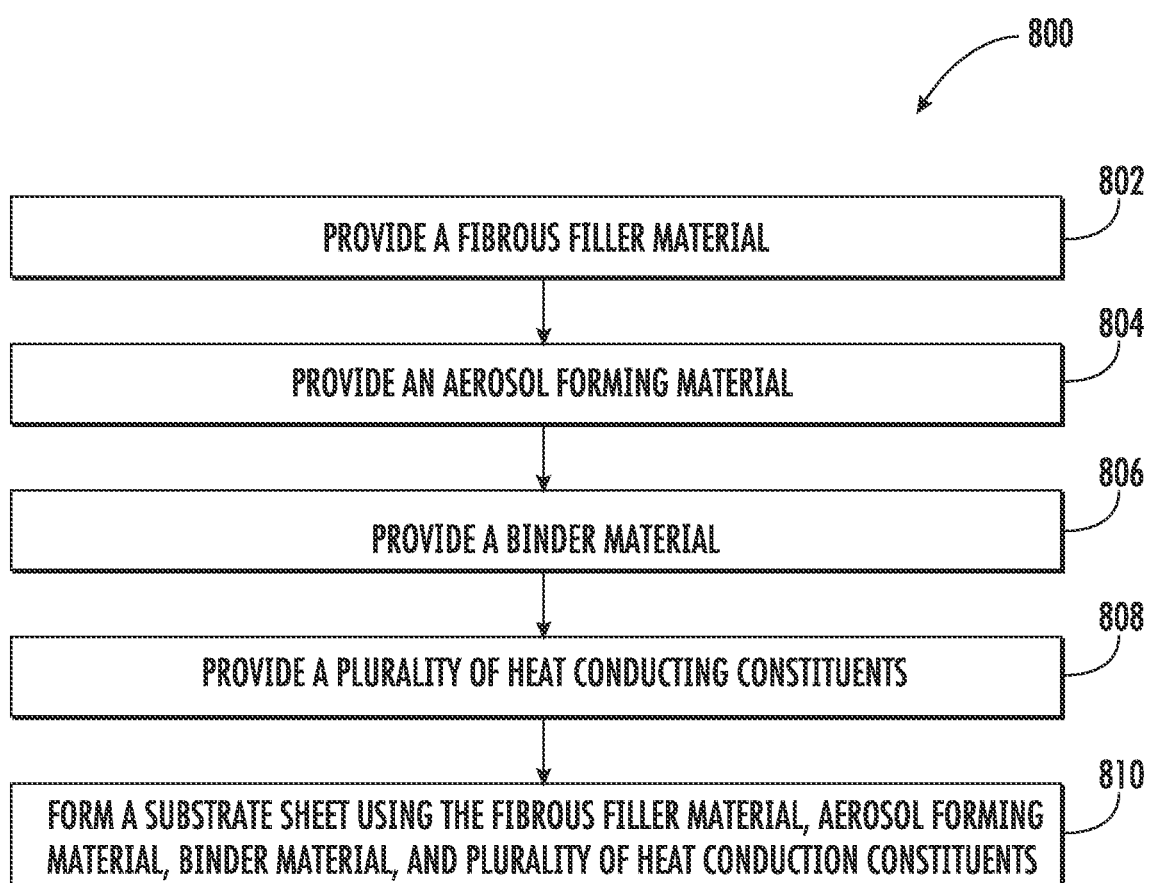
Figure 11:
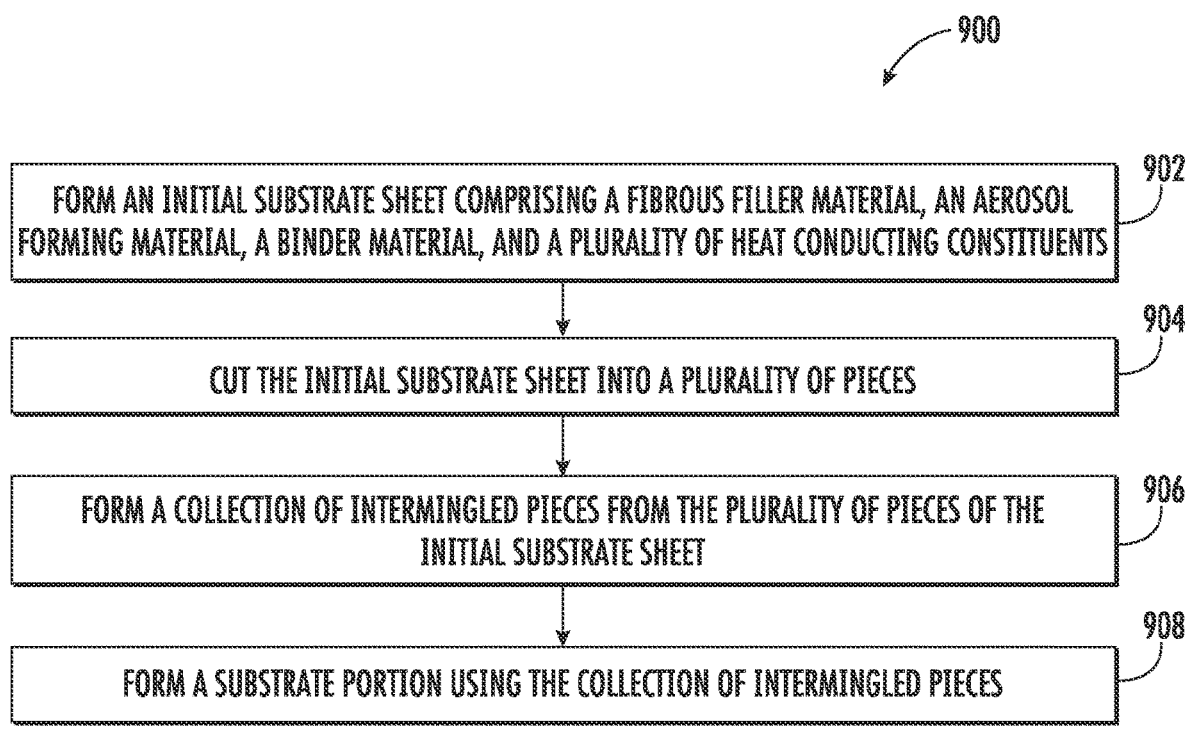
Figure 12:
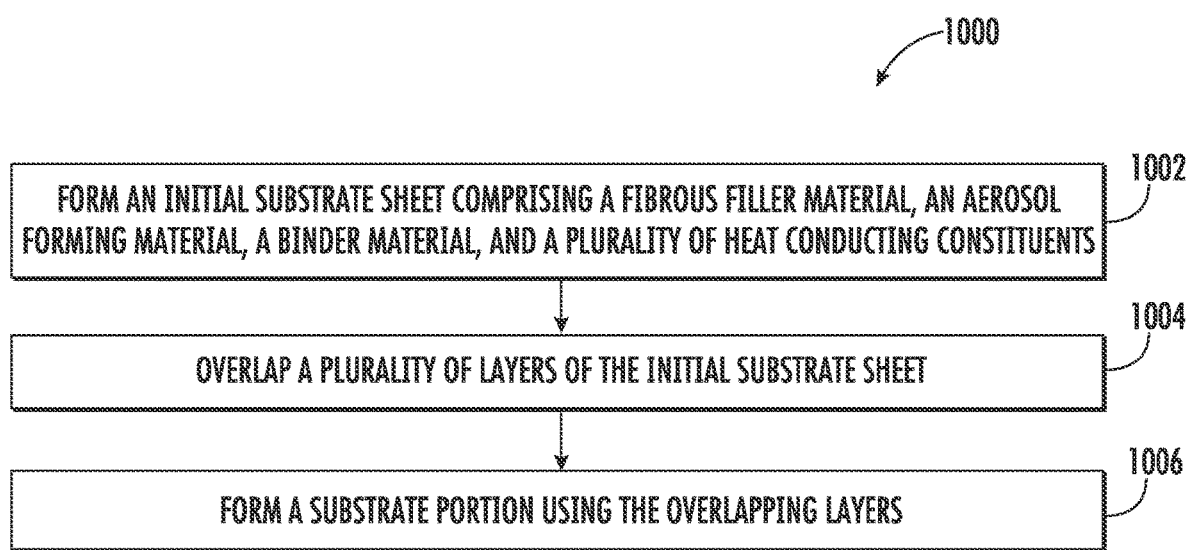
Figure 13:
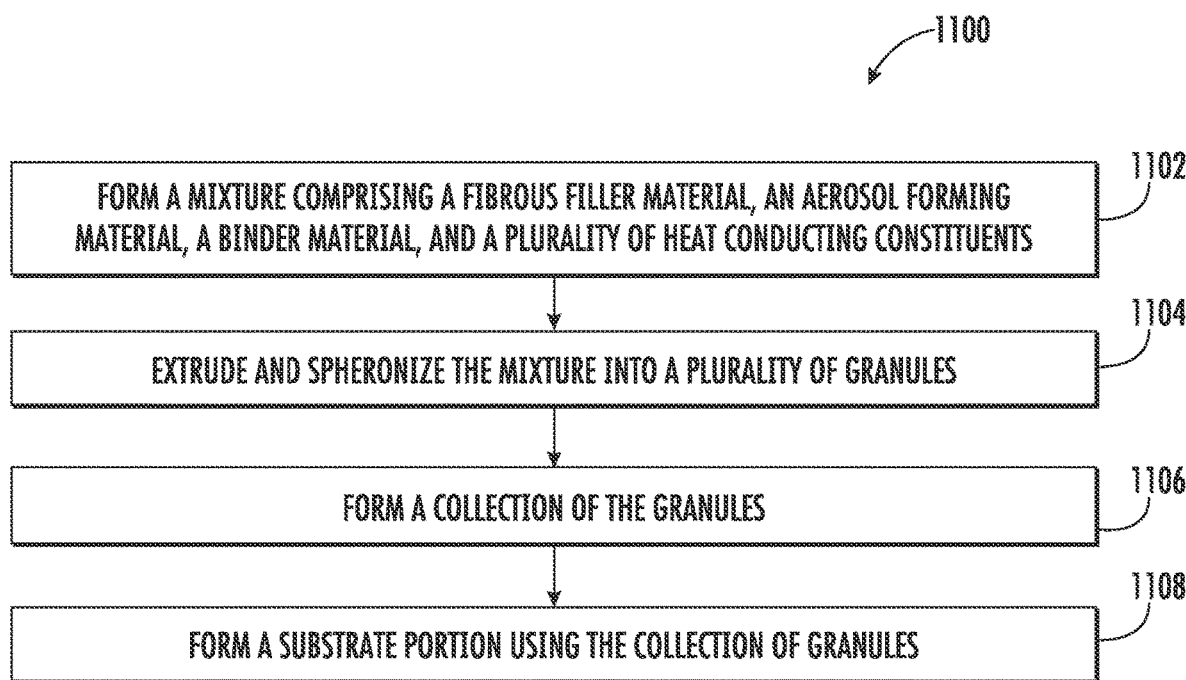
Figure 14:
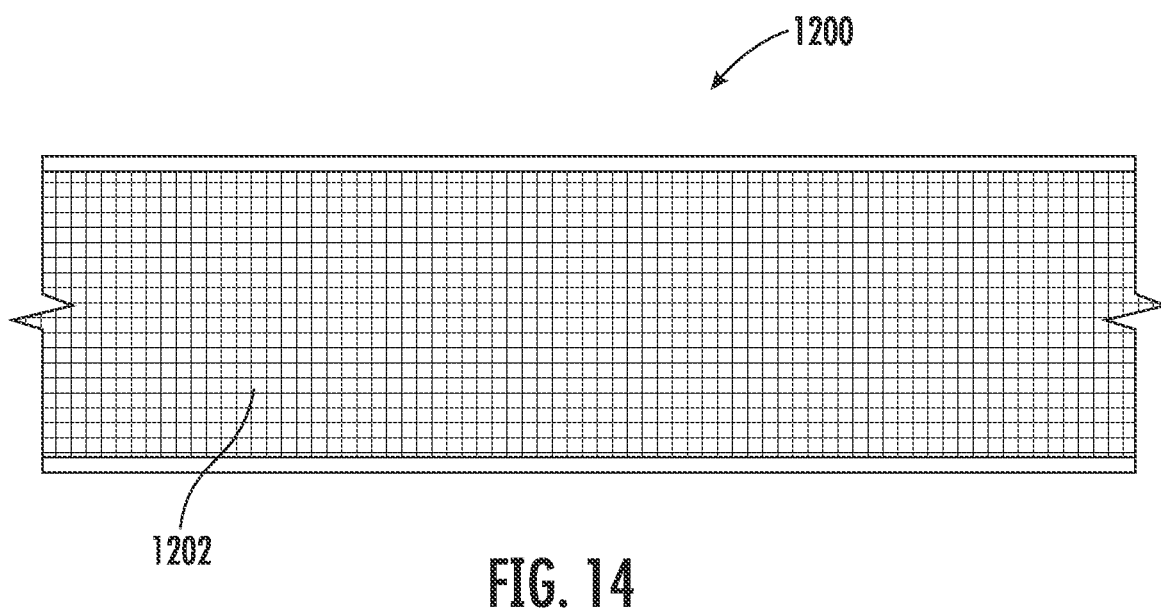
Figure 15:
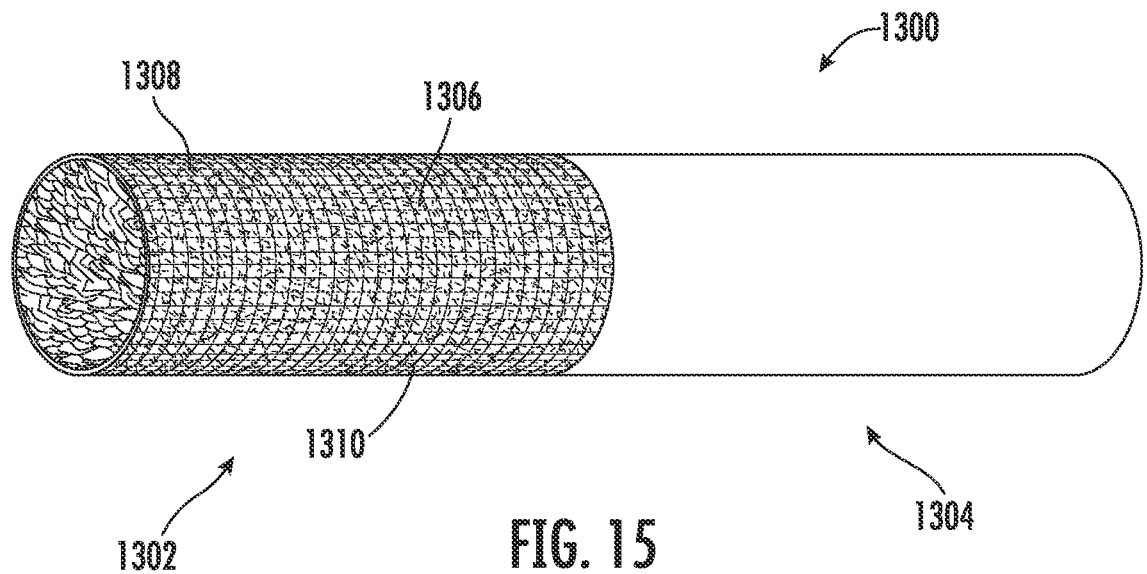
Figure 16:
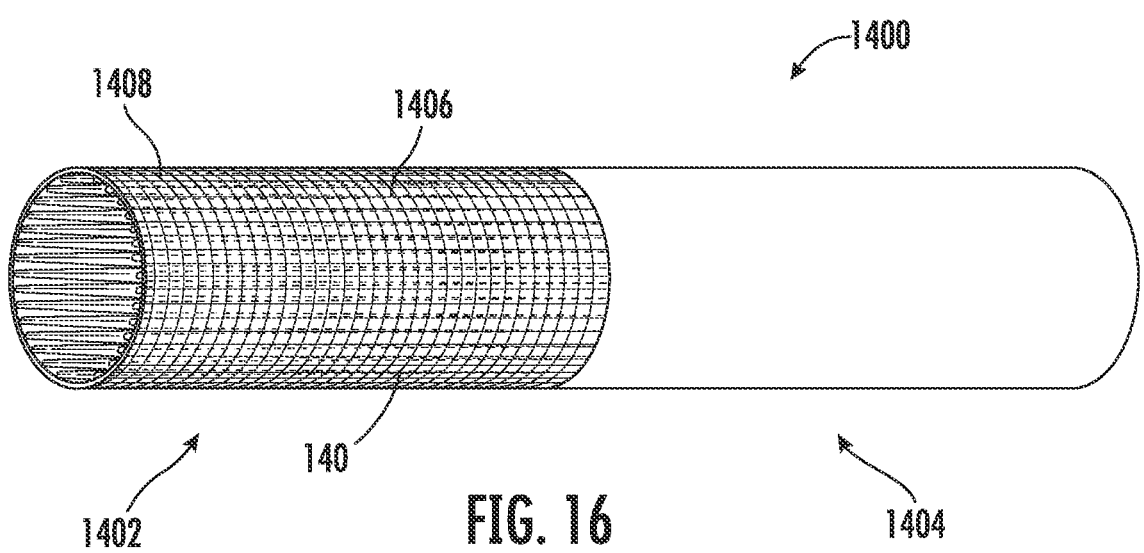

Having thus described aspects of the disclosure in the foregoing general terms, reference will now be made to the accompanying drawings, which are not necessarily drawn to scale, and wherein:

FIG. 1 illustrates a perspective view of an aerosol delivery device comprising a control body and an aerosol source member, wherein the aerosol source member and the control body are coupled to one another according to an example implementation of the present disclosure;

FIG. 2 illustrates a perspective view of the aerosol delivery device of FIG. 1 wherein the aerosol source member and the control body are decoupled from one another according to an example implementation of the present disclosure;

FIG. 3 illustrates a perspective view of an aerosol source member according to an example implementation of the disclosure;

FIG. 4 illustrates a schematic drawing of a substrate sheet according to an example implementation of the present disclosure;

FIG. 5 illustrates a schematic drawing of a substrate sheet according to an example implementation of the present disclosure;

FIG. 6 illustrates a schematic drawing of an aerosol source member according to an example implementation of the present disclosure;

FIG. 7 illustrates a schematic drawing of an aerosol source member according to an example implementation of the present disclosure;

FIG. 8 illustrates a schematic drawing of an aerosol source member according to an example implementation of the present disclosure;

FIG. 9 illustrates a schematic drawing of an aerosol source member according to an example implementation of the present disclosure;

FIG. 10 illustrates various operations in a method of manufacturing an aerosol generating substrate for use in an aerosol source member according to an example implementation of the present disclosure;

FIG. 11 illustrates various operations in a method of manufacturing an aerosol source member for use with an aerosol source delivery device according to an example implementation of the present disclosure;

FIG. 12 illustrates various operations in a method of manufacturing an aerosol source member for use with an aerosol source delivery device according to an example implementation of the present disclosure;

FIG. 13 illustrates various operations in a method of manufacturing an aerosol source member for use with an aerosol source delivery device according to an example implementation of the present disclosure;

FIG. 14 illustrates a schematic drawing of a substrate sheet according to an example implementation of the present disclosure;

FIG. 15 illustrates a schematic drawing of an aerosol source member according to an example implementation of the present disclosure; and FIG. 16 illustrates a schematic drawing of an aerosol source member according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol generating substrates for use in an aerosol source members and aerosol source members for use with aerosol delivery devices. Aerosol delivery devices according to the present disclosure use electrical energy to heat a material (preferably without combusting the material to any significant degree) to form an inhalable substance; and components of such systems have the form of articles that are sufficiently compact to be considered handheld devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes" or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some implementations, the terms may be interchangeable. Thus, for simplicity, the terms as used to describe aspects of the disclosure are understood to be interchangeable unless stated otherwise.

Aerosol delivery devices of the present disclosure generally include a number of components provided within an outer body or shell, which may be referred to as a housing. The overall design of the outer body or shell may vary, and the format or configuration of the outer body that may define the overall size and shape of the aerosol delivery device may vary. Typically, an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the aerosol delivery device are contained within one housing. Alternatively, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing aerosol source member). More specific formats, configurations and arrangements of components within the single housing type of unit or within a multi-piece separable housing type of unit will be evident in light of the further disclosure provided herein. Additionally, various aerosol delivery device designs and component arrangements may be appreciated upon consideration of the commercially available electronic aerosol delivery devices.

As will be discussed in more detail below, aerosol delivery devices of the present disclosure comprise some combination of a power source (i.e., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heater or heat generation member (e.g., an electrical resistance heating element or other component and/or an inductive coil or other associated components and/or one or more radiant heating elements), and an aerosol source member that includes a substrate portion capable of yielding an aerosol upon application of sufficient heat. In various implementations, the aerosol source member may include a mouth end or tip configured to allow drawing upon the aerosol delivery device for aerosol inhalation (e.g., a defined airflow path through the article such that aerosol generated can be withdrawn therefrom upon draw).

Alignment of the components within the aerosol delivery device of the present disclosure may vary across various implementations. In some implementations, the substrate material may be positioned proximate a heating element so as to maximize aerosol delivery to the user. Other configurations, however, are not excluded. Generally, the heating element may be positioned sufficiently near the substrate material so that heat from the heating element can volatilize the substrate material (as well as, in some implementations, one or more flavorants, medicaments, or the like that may likewise be provided for delivery to a user) and form an aerosol for delivery to the user. When the heating element heats the substrate material, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device of various implementations may incorporate a battery and/or other electrical power source to provide current flow sufficient to provide various functionalities to the aerosol delivery device, such as powering of a heating element, powering of control systems, powering of indicators, and the like. As will be discussed in more detail below, the power source may take on various implementations. Preferably, the power source may be able to deliver sufficient power to rapidly activate the heating member to provide for aerosol formation and power the aerosol delivery device through use for a desired duration of time. The power source is preferably sized to fit conveniently within the aerosol delivery device so that the aerosol delivery device can be easily handled. Examples of useful power sources include lithium-ion batteries that are preferably rechargeable (e.g., a rechargeable lithium-manganese dioxide battery). In particular, lithium polymer batteries can be used as such batteries can provide increased safety. Other types of batteries—e.g., N50-AAA CADNICA nickel-cadmium cells—may also be used. Additionally, a preferred power source is of a sufficiently light weight to not detract from a desirable smoking experience. Some examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

In another example, a personal vaporizer unit may comprise a first conductive surface configured to contact a first body part of a user holding the personal vaporizer unit, and a second conductive surface, conductively isolated from the first conductive surface, configured to contact a second body part of the user. As such, when the personal vaporizer unit detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

More specific formats, configurations and arrangements of various substrate materials, aerosol source members, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

In this regard, FIG. 1 illustrates an aerosol delivery device 100 according to an example implementation of the present disclosure. The aerosol delivery device 100 may include a control body 102 and an aerosol source member 104. In various implementations, the aerosol source member 104 and the control body 102 may be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like.

In various implementations, the aerosol delivery device 100 according to the present disclosure may have a variety of overall shapes, including, but not limited to an overall shape that may be defined as being substantially rod-like or substantially tubular shaped or substantially cylindrically shaped. In the implementations of FIGS. 1-3, the device 100 has a substantially round cross-section; however, other cross-sectional shapes (e.g., oval, square, triangle, etc.) also are encompassed by the present disclosure. Such language that is descriptive of the physical shape of the article may also be applied to the individual components thereof, including the control body 102 and the aerosol source member 104. In other implementations, the control body may take another hand-held shape, such as a small box shape.

In specific implementations, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the aerosol source member 104 may comprise a single-use device. A single use component for use with a control body is disclosed in U.S. Pat. No. 8,910,639 to Chang et al., which is incorporated herein by reference in its entirety.

In the depicted implementation, the aerosol source member 104 comprises a heated end 106, which is configured to be inserted into the control body 102, and a mouth end 108, upon which a user draws to create the aerosol. At least a portion of the heated end 106 may include a substrate portion 110. As discussed in more detail below, in some implementations the substrate portion 110 may comprise non-tobacco material, tobacco material, tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or semi-solid substrate. Representative types of solid and semi-solid constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein in their entireties. Other examples of substrates are described in U.S. Pat. App. Pub. No. 2013/0255702 to Griffith et al., the disclosure of which is incorporated herein by reference in its entirety.

In various implementations, the aerosol source member 104, or a portion thereof, may be wrapped in an exterior overwrap material 112 (see FIG. 3). In various implementations, the mouth end 108 of the aerosol source member 104 may include a filter 114, which may, for example, be made of a cellulose acetate or polypropylene material. The filter 114 may additionally or alternatively contain strands of tobacco containing material, such as described in U.S. Pat. No. 5,025,814 to Raker et al., which is incorporated herein by reference in its entirety. In various implementations, the filter 114 may increase the structural integrity of the mouth end of the aerosol source member, and/or provide filtering capacity, if desired, and/or provide resistance to draw. The exterior overwrap material may comprise a material that resists transfer of heat, which may include a paper or other fibrous material, such as a cellulose material. The exterior overwrap material may also include at least one filler material imbedded or dispersed within the fibrous material. In various implementations, the filler material may have the form of water insoluble particles. Additionally, the filler material may incorporate inorganic components. In various implementations, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth end 108 of the aerosol source member may function to simply separate the substrate portion 110 from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

In various implementations, other components may exist between the substrate portion 110 and the mouth end 108 of the aerosol source member 104, wherein the mouth end 108 may include a filter 114. For example, in some implementations one or any combination of the following may be positioned between the substrate portion 110 and the mouth end 108 of the aerosol source member 104: an air gap; a hollow tube structure; phase change materials for cooling air; flavor releasing media; ion exchange fibers capable of selective chemical adsorption; aerogel particles as filter medium; and other suitable materials.

As will be discussed in more detail below, the present disclosure is configured for use with a conductive and/or inductive heat source to heat a substrate material to form an aerosol. In various implementations, a conductive heat source may comprise a heating assembly that comprises a resistive heating element. Resistive heating elements may be configured to produce heat when an electrical current is directed therethrough. Electrically conductive materials useful as resistive heating elements may be those having low mass, low density, and moderate resistivity and that are thermally stable at the temperatures experienced during use. Useful heating elements heat and cool rapidly, and thus provide for the efficient use of energy. Rapid heating of the element may be beneficial to provide almost immediate volatilization of an aerosol precursor material in proximity thereto. Rapid cooling prevents substantial volatilization (and hence waste) of the aerosol precursor material during periods when aerosol formation is not desired. Such heating elements may also permit relatively precise control of the temperature range experienced by the aerosol precursor material, especially when time based current control is employed. Useful electrically conductive materials are preferably chemically non-reactive with the materials being heated (e.g., aerosol precursor materials and other inhalable substance materials) so as not to adversely affect the flavor or content of the aerosol or vapor that is produced. Exemplary, non-limiting, materials that may be used as the electrically conductive material include carbon, graphite, carbon/graphite composites, metals, ceramics such as metallic and non-metallic carbides, nitrides, oxides, silicides, intermetallic compounds, cermets, metal alloys, and metal foils. In particular, refractory materials may be useful. Various, different materials can be mixed to achieve the desired properties of resistivity, mass, and thermal conductivity. In specific implementations, metals that can be utilized include, for example, nickel, chromium, alloys of nickel and chromium (e.g., nichrome), and steel. Materials that can be useful for providing resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

In various implementations, the heating member may be provided in a variety forms, such as in the form of a foil, a foam, a mesh, a hollow ball, a half ball, discs, spirals, fibers, wires, films, yarns, strips, ribbons, or cylinders. Such heating elements often comprise a metal material and are configured to produce heat as a result of the electrical resistance associated with passing an electrical current therethrough. Such resistive heating elements may be positioned in proximity to, and/or in direct contact with, the substrate portion. The heating assembly or the heating member may be located in the control body and/or the aerosol source member, as will be discussed in more detail below. In various implementations, the substrate portion may include components (i.e., heat conducting constituents) that are imbedded in, or otherwise part of, the substrate portion that may serve as, or facilitate the function of, the heating assembly. Some examples of various heating members and elements are described in U.S. Pat. No. 9,078,473 to Worm et al., the disclosure of which is incorporated herein by reference in its entirety.

Some non-limiting examples of various heating member configurations include configurations in which a heating member or element is placed in proximity with an aerosol source member. For instance, in some examples, at least a portion of a heating member may surround at least a portion of an aerosol source member. In other examples, one or more heating members may be positioned adjacent an exterior of an aerosol source member when inserted in a control body. In other examples, at least a portion of a heating member may penetrate at least a portion of an aerosol source member (such as, for example, one or more prongs and/or spikes that penetrate an aerosol source member), when the aerosol source member is inserted into the control body.

In various implementations, the heating member may take a variety of forms. For example, in one implementation, the heating member may comprise a cylinder or other heating device located in the control body 102. In various implementations, the heating member may be constructed of one or more conductive materials, including, but not limited to, copper, aluminum, platinum, gold, silver, iron, steel, brass, bronze, carbon (e.g., graphite), or any combination thereof. In various implementations, the heating member may also be coated with any of these or other conductive materials. The heating member may be located proximate an engagement end of the control body 102, and may be configured to substantially surround a portion of the heated end 106 of the aerosol source member 104 that includes the substrate portion 110. In such a manner, the heating member may be located proximate the substrate portion 110 of the aerosol source member 104 when the aerosol source member is inserted into the control body 102.

As will be discussed in more detail below, in various implementations, one or more heat conducting constituents may be located within and/or on the surface of a substrate. While in some implementations, the substrate may comprise a sheet, in other implementations the substrate may take a variety of different forms. In various implementations, the substrate may be used to create a substrate portion of an aerosol source member. As such, in various implementations, when the heating member is heated, the heat conducting constituents increase heat conduction within the substrate portion. Although in some implementations the heating member may comprise a cylinder, it should be noted that in other implementations, the heating member may take a variety of forms and, in some implementations, may make direct contact with and/or penetrate the substrate portion.

As described above, in addition to being configured for use with a conductive heat source, the present disclosure may also be configured for use with an inductive heat source to heat a substrate portion to form an aerosol. In various implementations, an inductive heat source may comprise a resonant transformer, which may comprise a resonant transmitter and a resonant receiver (e.g., a susceptor). In some implementations, the resonant transmitter may be located in the control body 102 and the substrate portion may include heat conducting constituents that comprise the resonant receiver. In other implementations, the heat conducting constituents may facilitate the function of a separate resonant receiver, or may provide an additional resonant receiver.

For example, in some implementations, the control body 102 may include a resonant transmitter, which, for example, may comprise a foil material, a coil, a cylinder, or other structure configured to generate an oscillating magnetic field. In some implementations, the heat conducting constituents of the substrate portion may comprise the resonant receiver such that an alternating current is induced in the heat conducting constituents of the substrate portion. In other implementations, the heat conducting constituents of the substrate portion may facilitate the function of a separate resonant receiver or may serve as a second resonant receiver such that an alternating current is induced in the heat conducting constituents in addition to a separate resonant receiver that, in some implementations, may be located in the control body 102. For example, in various implementations, a resonant receiver located in the control body 102 may comprise one or more prongs that extend into the substrate portion or are surrounded by the substrate portion. Other possible resonant transformer components, including resonant transmitters and resonant receivers, are described in U.S. patent application Ser. No. 15/799,365, filed on Oct. 31, 2017, which is incorporated herein by reference in its entirety.

In other implementations, a resonant transmitter may comprise a helical coil configured to circumscribe a cavity into which an aerosol source member, and in particular, a substrate portion of an aerosol source member, is received. In some implementations, the helical coil may be located between an outer wall of the device and the receiving cavity. In one implementation, the coil winds may have a circular cross section shape; however, in other implementations, the coil winds may have a variety of other cross section shapes, including, but not limited to, oval shaped, rectangular shaped, L-shaped, T-shaped, triangular shaped, and combinations thereof. In another implementation, a pin may extend into a portion of the receiving cavity, wherein the pin may comprise the resonant transmitter, such as by including a coil structure around or within the pin. In various implementations, an aerosol source member may be received in the receiving cavity wherein one or more components of the aerosol source member may serve as the resonant receiver. For example, in some implementations, the heat conducting constituents of the substrate portion may comprise the resonant receiver. In other implementations, the heat conducting constituents may facilitate the function of a separate resonant receiver (such as, for example, a pin, rod, and/or receiver particles) that are located in the aerosol source member.

As noted above, in various implementations of the present disclosure, an aerosol source member may comprise a substrate portion that includes a substrate material. In various implementations, the substrate material may comprise a substrate sheet. FIG. 4 is a schematic drawing of a substrate sheet 200 according to an example implementation of the present disclosure. In particular, FIG. 4 illustrates a cast substrate sheet 200 comprising an aerosol generating substrate. In the particular implementation illustrated in FIG. 4, the substrate sheet 200 comprises a mixture of a fibrous filler material, an aerosol forming material, a binder material, and a plurality of heat conducting constituents. In some implementations, the fibrous filler material may comprise a plant-derived, non-tobacco material such as a cellulose pulp material. In other implementations, the non-tobacco filler material may not be a plant-derived material.

In various implementations, tobacco materials that may be useful in the present disclosure can vary and may include, for example, flue-cured tobacco, burley tobacco, Oriental tobacco or Maryland tobacco, dark tobacco, dark-fired tobacco and Rustica tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT Pat. App. Pub. No. WO 02/37990 to Bereman; and Bombick et al., Fund. Appl. Toxicol., 39, p. 11-17 (1997); which are incorporated herein by reference in their entireties. Further exemplary tobacco compositions that may be useful are disclosed in U.S. Pat. No. 7,726,320 to Robinson et al., which is incorporated herein by reference in its entirety.

In various implementations, the filler material may comprise other fibrous materials, including, but not limited to, hemp, flax, sisal, rice straw, and/or esparto. In various other implementations, the filler material may comprise reconstituted tobacco by itself or combined with other filler materials. Exemplary manners and methods for providing a reconstituted tobacco sheet, including casting and papermaking techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety. In some instances, processed tobaccos, such as certain types of reconstituted tobaccos, can be employed as longitudinally extending strands. See, for example, the type of configuration set forth in U.S. Pat. No. 5,025,814 to Raker, which is incorporated herein by reference in its entirety. In addition, certain types of reconstituted tobacco sheets can be formed, rolled, or gathered into a desired configuration. In still other implementations, the fibrous material may comprise inorganic fibers of various types (e.g., fiber glass, metal wires/screens, etc.) and/or (organic) synthetic polymers. In various implementations, these "fibrous" materials could be unstructured (e.g., randomly distributed like the cellulose fibers in tobacco cast sheet) or structured (e.g., a wire mesh).

In some implementations, the aerosol forming material may comprise glycerin or propylene glycol. Preferred aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety.

As noted above, the present disclosure incorporates a binder material. In the depicted implementation, the binder material comprises an ammonium alginate. Preferred binder materials include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethylcellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass. In some other implementations, the binder may include a cyclodextrin.

Some implementations may further comprise additional components, such as, for example, a heat or flame/burn retardant material such as ammonium phosphate. In some implementations, other flame/burn retardant materials and additives may be included within the substrate sheet and my include organo-phosphorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the substrate material and/or other components (whether alone or in combination with each other and/or other materials), the desirable properties are preferably provided without undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties. Additional additives, and other possible enhancing constituents are described in U.S. patent application Ser. No. 15/707,461 to Phillips et al., which is incorporated herein by reference in its entirety.

The aerosol generating substrate may also include a plurality of heat conducting constituents. In various implementations, the heat conducting constituents may be made of a metal material, a metal alloy material, a ceramic material, a polymeric fiber material coated with a metal material, a carbon material (e.g., graphite), or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a plurality of metal fibers 202 that are mixed with the other components of the substrate sheet 200 (e.g., the fibrous filler material, aerosol forming material, and binder material). In some implementations, the substrate material may comprise a cast sheet, into and/or onto which the heat conducting constituents are included. In other implementations, the substrate material may comprise a combination of a cast sheet and reconstituted tobacco, into and/or onto which the heat conducting constituents are included. In still other implementations, the substrate material may comprise reconstituted tobacco, into and/or onto which the heat conducting constituents are included. In particular, in some implementations, the substrate material may comprise approximately 75%-100% (and in some implementations, approximately 90%) cast sheet and approximately 0%-25% (and in some implementations, approximately 10%) reconstituted tobacco, in addition to the heat conducting constituents. In other implementations, the substrate material may comprise approximately 100% reconstituted tobacco, in addition to the heat conducting constituents. In various implementations, the amount of the heat conducting constituents and/or the amount of the non-conducting materials may vary according to specific requirements of the substrate material and/or an aerosol source member incorporating the substrate material.

Likewise, in various implementations the relative amounts of the elements within each component may vary according to specific requirements of the substrate material and/or an aerosol source member incorporating the substrate material. For example, in one example implementation that includes a cast sheet component and a reconstituted tobacco component, the amount of aerosol forming material (e.g., glycerin) in the cast sheet component may be approximately 30%-60%, and the amount of aerosol forming material (e.g., glycerin) in the reconstituted tobacco component may be approximately 10%-25%. In another example implementation that includes approximately 100% reconstituted tobacco, the amount of aerosol forming material (e.g., glycerin) may be approximately 5%-40%, and the amount of aerosol forming material (e.g., glycerin) in the reconstituted tobacco component may be approximately 10%-25%.

In the depicted example implementation, the non-heat conducting components of the substrate sheet 200 may comprise approximately 38% cut tobacco, approximately 53% glycerin, approximately 6% ammonium alginate, and approximately 3% ammonium phosphate. In another related, but non-tobacco implementation, the substrate sheet 200 may comprise approximately 38% cellulose pulp, approximately 53% glycerin, approximately 6% ammonium alginate, and approximately 3% ammonium phosphate. In still another related implementation, the substrate sheet may comprise approximately 90% reconstituted tobacco, approximately 8% cellulose pulp, and approximately 2% potassium carbonate. In some implementations, the reconstituted tobacco may have an aerosol forming material absorbed and/or loaded into it. For example, some implementations may have glycerin loaded into the reconstituted tobacco at, or within a range of 20%-50%. Regardless of the composition of the rest of the mixture, it should be noted that the amount of heat conducting constituents added to the mixture may vary according to various implementations, and thus the relative amount of the heat conducting constituents may be adjusted to meet particular requirements. It should be noted that the heat conducting constituents, as well as any of the other portions or components of the substrate materials and aerosol source members represented in the figures of the present disclosure, are depicted as such for ease of illustration, and thus the relative size and shape of the heat conducting constituents, and the other portions or components of the substrate materials and aerosol source members, are not necessarily representative of the size and shape of such elements in practice.

In any event, in some implementations the substrate sheet 200 may be constructed via a casting process, such as that described in U.S. Pat. No. 5,697,385, to Seymour et al., the disclosure of which is incorporated herein by reference in its entirety. For example, the fibrous filler material, aerosol forming material, binder material, and the plurality of heat conducting constituents may be blended together to form a slurry, which may be cast onto a surface (such as, for example, a moving belt). The cast slurry may then experience one or more drying and/or doctoring steps such that the result is a relatively consistent thickness sheet. In the case of the depicted implementation, the resulting substrate sheet 200 includes the plurality of metal fibers 202 randomly (or substantially randomly) distributed within the thickness of the substrate sheet 200. In such a manner, by substantially randomly distributing the heat conducting constituents within the substrate sheet, heat conduction of the substrate sheet (or a substrate portion created from the substrate sheet), may be increased in all directions. Other examples of casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,706 to Kumar; the disclosures of which is incorporated herein by reference in their entireties.

FIG. 5 is a schematic drawing of a substrate sheet 300 according to another example implementation of the present disclosure. In particular, FIG. 5 illustrates a cast substrate sheet 300 comprising the aerosol generating substrate. In the particular implementation illustrated in FIG. 5, the substrate sheet 300 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a carbon material (e.g., graphite), a polymeric fiber material coated with a metal material, and/or any combination thereof. In addition, in various implementations, the plurality of heat conducting constituents may take a granular form, a powder form, a fiber form, a mesh, a fiber cloth, and/or any combination thereof.

In the depicted implementation, the heat conducting constituents comprise a series of bands 302, separated by a series of spaces 304 in between, such that a segmented pattern is formed. Furthermore, in the depicted implementation, the series of bands 302 comprising the heat conducting constituents are formed on the surface of the substrate sheet 300. It should be noted that although the bands 302 are shown substantially transverse to a longitudinal axis of the sheet 300, in other implementations, bands may be configured at any angle with respect to a longitudinal axis of the sheet, including, for example, substantially parallel to a longitudinal axis of the sheet or angled with respect to a longitudinal axis of the sheet. As such, and as will be discussed in more detail below, in various implementations of an aerosol source member in which a substrate sheet is used as an overwrap substrate sheet, the resulting bands may have any orientation with respect to a longitudinal axis of the aerosol source member, including, for example, substantially transverse to a longitudinal axis of the aerosol source member (see, e.g., FIGS. 8 and 9) or, for example, substantially parallel to a longitudinal axis of the aerosol source member or angled with respect to a longitudinal axis of the source member.

In various implementations, prior to addition of the heat conducting constituents, the substrate sheet 300 may be constructed as noted above. For example, although the relative amounts of the other (i.e., non-heat conducting constituent) components of the substrate sheet 300 may vary, in the some implementations, these components of the substrate sheet 300 may comprise approximately 38% cut tobacco, approximately 53% glycerin, approximately 6% ammonium alginate, and approximately 3% ammonium phosphate. In other implementations, the sheet 300 may comprise approximately 38% cellulose pulp, approximately 53% glycerin, approximately 6% ammonium alginate, and approximately 3% ammonium phosphate. As noted above, in some implementations, the substrate sheet 300 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet. As noted above, regardless of the composition of the rest of the mixture, it should be noted that the amount of heat conducting constituents added to the mixture may vary according to various implementations, and thus the relative amount of the heat conducting constituents may be adjusted to meet particular requirements.

In various implementations, the segmented pattern may be created in a variety of ways, including, for example, by selective adhesion, metal printing, lamination, and/or stitching onto the formed substrate sheet 300. For example, in one implementation, the bands 302 may be created by selective powder coating of a heat conducting constituents onto a surface of the substrate sheet 300. In another implementation, the bands 302 may be created by electrostatically attracting the heat conducting constituents to a surface of the substrate sheet 300 and adhering the material in the segmented pattern to the substrate sheet 300. In another implementation, the bands 302 may be created using a masking template. In another implementation, the bands 302 may be created by printing a conductive metal material (i.e., the heat conducting constituents) onto a surface of the substrate sheet 300 in the segmented pattern. In another implementation, the heat conducting constituents (for example, in the form of conductive yarns) may be stitched into the surface of the substrate sheet 300 such that the segmented pattern is formed. In such a manner, by positioning the heat conducting constituents in a segmented pattern on the substrate sheet, heat conduction of the substrate sheet or a substrate portion created from the substrate sheet, may be increased in a unidirectional manner.

FIG. 14 is a schematic drawing of a substrate sheet 1200 according to another example implementation of the present disclosure. In particular, FIG. 14 illustrates a cast substrate sheet 1200 comprising the aerosol generating substrate. In the particular implementation illustrated in FIG. 14, the substrate sheet 1200 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a carbon material (e.g., graphite), a polymeric fiber material coated with a metal material, and/or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a metal mesh 1202 that is laminated onto the substrate sheet 1200. It should be noted that although the mesh 1202 is shown such that its pattern is substantially aligned with a longitudinal axis of the sheet 1200, in other implementations, the mesh may be configured at any angle with respect to a longitudinal axis of the sheet. As such, and as will be discussed in more detail below, in various implementations of an aerosol source member in which a substrate sheet is used as an overwrap substrate sheet, the mesh may have any orientation with respect to a longitudinal axis of the aerosol source member.

In various implementations, prior to addition of the heat conducting constituents, the substrate sheet 1200 may be constructed as noted above. For example, although the relative amounts of the other (i.e., non-heat conducting constituent) components of the substrate sheet 1200 may vary, in the some implementations, these components of the substrate sheet 300 may comprise approximately 38% cut tobacco, approximately 53% glycerin, approximately 6% ammonium alginate, and approximately 3% ammonium phosphate. In other implementations, the sheet 300 may comprise approximately 38% cellulose pulp, approximately 53% glycerin, approximately 6% ammonium alginate, and approximately 3% ammonium phosphate. As noted above, in some implementations, the substrate sheet 1200 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet. As noted above, regardless of the composition of the rest of the mixture, it should be noted that the amount of heat conducting constituents added to the mixture may vary according to various implementations, and thus the relative amount of the heat conducting constituents may be adjusted to meet particular requirements.

FIG. 6 is a schematic drawing of an aerosol source member 400 according to an example implementation of the present disclosure. In the depicted implementation, the aerosol source member 400 includes a substrate portion 402 and a mouth end portion 404. In various implementations, the substrate portion 402 may comprise a collection of intermingled pieces 406 that are cut from an initial substrate sheet. For example, in the depicted implementation, the collection of intermingled pieces 406 are cut from an initial substrate sheet similar to, or substantially the same as, the substrate sheet 200 described above with respect to FIG. 4. As such, the composition and construction of the individual pieces 406 may be similar to, or substantially the same as, that described above with respect to the substrate sheet 200. In particular, the intermingled pieces 406 of the depicted implementation may start as an initial substrate sheet that comprises a mixture of a fibrous filler material, an aerosol forming material, a binder material, and a plurality of heat conducting constituents. Reference is made to the discussion above with respect to various possible filler materials, aerosol forming materials, binder materials, and heat conducting constituents for use in the initial substrate sheet, and possible relative amounts of each. The initial substrate sheet may then be cut into a plurality of pieces (e.g., strips, sections, portions, etc.) and collected for use as the substrate portion 402 of the aerosol source member 400. In various implementations, the initial substrate sheet may be cut in a variety of different ways. For example, in one implementation, the initial substrate sheet may be cut via a mechanical cutting machine (e.g., a guillotine device and/or a paper shredding machine). In other implementations, the initial substrate sheet may be cut via a laser cutting and/or a waterjet cutting device. In other implementations, the initial substrate sheet may be fibrillated. In other implementations, a hammer mill may be used to reduce the initial substrate sheet size and then the resulting sheet may be subsequently cut using one or more of the methods described above.

As described above, in some implementations, the initial substrate sheet may be constructed via a casting process, wherein the fibrous filler material, aerosol forming material, binder material, and plurality of heat conducting constituents may be blended together to form a slurry, which may be cast onto a surface (such as, for example, a moving belt). The cast slurry may then experience one or more drying and/or doctoring steps such that the result is a relatively consistent thickness initial sheet. In the case of the depicted implementation, the resulting initial sheet may include a plurality of metal fibers randomly (or substantially randomly) distributed within the thickness of the sheet.

In various implementations, the mouth end portion 404 of the aerosol source member 400 may comprise a variety of materials, which, in some implementations, may include a filter, as described above. Other materials that may be located in the mouth end portion 404, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. In various implementations, tobacco blends may comprise various types and forms of tobaccos in a blended cut filler form. For example, certain popular tobacco blends for cigarette manufacture, commonly referred to as "American blends," comprise mixtures of cut or shredded pieces of flue-cured tobacco, burley tobacco and Oriental tobacco; and such blends, in many cases, also contain pieces of processed tobaccos, such as processed tobacco stems, volume expanded tobaccos and/or reconstituted tobaccos. The precise amount of each type or form of tobacco within a tobacco blend used for the manufacture of a particular smoking article can vary, and is a manner of design choice, depending upon factors such as the sensory characteristics (e.g., flavor and aroma) that are desired. See, for example, the types of tobacco blends described in Tobacco Encyclopedia, Voges (Ed.) p. 44-45 (1984), Browne, The Design of Cigarettes, 3.sup.rd Ed., p. 43 (1990) and Tobacco Production, Chemistry and Technology, Davis et al. (Eds.) p. 346 (1999). See, also, the representative types of tobacco blends set forth in U.S. Pat. No. 4,836,224 to Lawson et al.; U.S. Pat. No. 4,924,888 to Perfetti et al.; U.S. Pat. No. 5,056,537 to Brown et al.; and U.S. Pat. No. 5,220,930 to Gentry; U.S. Patent App. Pub. Nos. 2004/0255965 to Perfetti et al.; and 2005/0066986 to Nestor et al.; PCT App. Pub. No. WO 02/37990 to Bereman; and Bombick et al., Fund. Appl. Toxicol., 39, p. 11-17 (1997); each of which is incorporated herein by reference in its entirety.

As used herein, reference to a "flavorant" refers to compounds or components that can be aerosolized and delivered to a user and which impart a sensory experience in terms of taste and/or aroma. Exemplary flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Exemplary plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

Some examples of suitable phase change materials include, but are limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

FIG. 7 is a schematic drawing of an aerosol source member 500 according to an example implementation of the present disclosure. In the depicted implementation, the aerosol source member 500 includes a substrate portion 502 and a mouth end portion 504. In various implementations, the substrate portion 502 may comprise a series of overlapping layers 506 of an initial substrate sheet (e.g., a gathered web comprising an initial substrate sheet). For example, in the depicted implementation, the series of overlapping layers 506 comprises a series of layers of an initial substrate sheet similar to, or substantially the same as, the substrate sheet 200 described above with respect to FIG. 4. In another example implementation, the series of overlapping layers 506 of an initial substrate sheet may be similar to, or substantially the same as, the substrate sheet 1200 of FIG. 14. As such, the composition and construction of the layers may be similar to, or substantially the same as, that described above with respect to the substrate sheet 200 or sheet 1200. In particular, the overlapping layers of the depicted implementation may start as an initial substrate sheet that comprises a mixture of a fibrous filler material, an aerosol forming material, a binder material, and a plurality of heat conducting constituents. Reference is made to the discussion above with respect to various possible filler materials, aerosol forming materials, binder materials, and heat conducting constituents for use in the initial substrate sheet, and possible relative amounts of each. The initial substrate sheet may then be folded into an overlapping manner (e.g., gathered web) for use as the substrate portion 502 of the aerosol source member 500. It should be noted that in various implementations, the term "overlapping layers" may also include bunched, crumped, and/or otherwise gathered layers in which the individual layers may not be obvious.

In various implementations, the mouth end portion 504 may comprise a variety of materials, which, in some implementations, may include a filter, as described above. Other materials that may be located in the mouth end portion, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. Reference is made to the discussion of these components above with respect to FIG. 6.

FIG. 8 is a schematic drawing of an aerosol source member 600 according to an example implementation of the present disclosure. In the depicted implementation, the aerosol source member 600 includes a substrate portion 602, a mouth end portion 604, and an overwrap substrate sheet 608 extending around at least a portion of the substrate portion 602. In various implementations, the overwrap substrate sheet 608 may be separate from an optional exterior overwrap material, as discussed above. In various implementations, the substrate portion 602 may comprise a collection of intermingled pieces 606 that are cut from an initial substrate sheet. For example, in the depicted implementation, the collection of intermingled pieces 606 are cut from an initial substrate sheet similar to, or substantially the same as, the substrate sheet 200 described above with respect to FIG. 4. As such, the composition and construction of the individual pieces 606 may be the similar to, or substantially the same as, that described above with respect to the sheet 200. In particular, the intermingled pieces 606 of the depicted implementation may start as an initial substrate sheet that comprises a mixture of a fibrous filler material, an aerosol forming material, a binder material, and a plurality of heat conducting constituents. Reference is made to the discussion above with respect to various possible filler materials, aerosol forming materials, binder materials, and heat conducting constituents for use in the initial substrate sheet and possible relative amounts of each. The initial substrate sheet may then be cut into a plurality of pieces (e.g., strips, sections, portions, etc.) and collected for use as the substrate portion 602 of the aerosol source member 600.

As described above, in some implementations, the initial substrate sheet may be constructed via a casting process, wherein the fibrous filler material, aerosol forming material, binder material, and plurality of heat conducting constituents may be blended together to form a slurry, which may be cast onto a surface (such as, for example, a moving belt). The cast slurry may then experience one or more drying and/or doctoring steps such that the result is a relatively consistent thickness initial sheet. In the case of the depicted implementation, the resulting initial sheet may include a plurality of metal fibers randomly (or substantially randomly) distributed within the thickness of the sheet.

As noted above, the aerosol source member 600 of the depicted implementation also includes an overwrap substrate sheet 608 that extends around at least a portion of the substrate portion 602. In the depicted implementation, the overwrap substrate sheet 608 is similar to, or substantially the same as, the substrate sheet 300 described above with respect to FIG. 5. As such, the composition and construction of the overwrap substrate sheet 608 may be similar to, or substantially the same as, that described above with respect to the substrate sheet 300. For example, in the depicted implementation, the overwrap substrate sheet 608 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a polymeric fiber material coated with a metal material, or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a series of bands 612, separated by a series of spaces 614 in between, such that a segmented pattern is formed. Furthermore, in the depicted implementation, the series of bands 612 that comprise the heat conducting constituents are formed on the surface of the overwrap substrate sheet 608. Further reference is made to the discussion above with respect to various possible filler materials, aerosol forming materials, binder materials, and heat conducting constituents for use in the initial substrate sheet, and possible relative amounts of each.

As noted above, in some implementations, the overwrap substrate sheet 608 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet.

In various implementations, the segmented pattern may be created in a variety of ways, including, for example, by selective adhesion, metal printing, lamination, and/or stitching onto the formed overwrap sheet 608. For example, in one implementation, the bands 612 may be created by selective powder coating of a heat conducting material onto a surface of the overwrap substrate sheet 608. In another implementation, the bands 612 may be created by electrostatically attracting the heat conducting material to a surface of the overwrap substrate sheet 608 and adhering the material in the segmented pattern to the overwrap substrate sheet 608. In another implementation, the bands 612 may be created using a masking template. In another implementation, the bands 612 may be created by printing a conductive metal material onto a surface of the overwrap substrate sheet 608 in the segmented pattern. In another implementation, the heat conducting material (for example, in the form of conductive yarns) may be stitched into the surface of the overwrap substrate sheet 608 such that the segmented pattern is formed. As noted above, in various implementations of an aerosol source member in which a substrate sheet is used as an overwrap substrate sheet, the resulting bands may have any orientation with respect to a longitudinal axis of the aerosol source member, including, for example, bands that are substantially transverse to a longitudinal axis of the aerosol source member, such as the depicted implementation. In other implementations, the bands may have any other angle with respect to a longitudinal axis of the aerosol source member, including, for example, substantially parallel to a longitudinal axis of the aerosol source member or angled with respect to a longitudinal axis of the aerosol source member.

In various implementations, the mouth end portion 604 may comprise a variety of materials, which, in some implementations, may include a filter, as described above. Other materials that may be located in the mouth end portion, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. Reference is made to the discussion of these components above with respect to FIG. 6.

FIG. 9 is a schematic drawing of an aerosol source member 700 according to an example implementation of the present disclosure. In the depicted implementation, the aerosol source member 700 includes a substrate portion 702, a mouth end portion 704, and an overwrap substrate sheet 708 extending around at least a portion of the substrate portion 702. In various implementations, the overwrap substrate sheet 708 may be separate from an optional exterior overwrap material, as discussed above. In various implementations, the substrate portion 702 may comprise a series of overlapping layers 706 of an initial substrate sheet (e.g., a gathered web comprising an initial substrate sheet). For example, in the depicted implementation, the series of overlapping layers 706 comprises layers of an initial substrate sheet similar to, or substantially the same as, the substrate sheet 200 described above with respect to FIG. 4. In another example implementation, the series of overlapping layers 506 of an initial substrate sheet may be similar to, or substantially the same as, the substrate sheet 1200 of FIG. 14. As such, the composition and construction of the layers may be similar to, or substantially the same as, that described above with respect to the sheet 200 or sheet 1200. In particular, the overlapping layers of the depicted implementation may start as an initial substrate sheet that comprises a mixture of a fibrous filler material, an aerosol forming material, a binder material, and a plurality of heat conducting constituents. Reference is made to the discussion above with respect to various possible filler materials, aerosol forming materials, binder materials, and heat conducting constituents for use in the initial substrate sheet and possible relative amounts of each.

As described above, in some implementations, the initial substrate sheet may be constructed via a casting process, wherein the fibrous filler material, aerosol forming material, binder material, and plurality of heat conducting constituents may be blended together to form a slurry, which may be cast onto a surface (such as, for example, a moving belt). The cast slurry may then experience one or more drying and/or doctoring steps such that the result is a relatively consistent thickness initial sheet. In the case of the depicted implementation, the resulting initial sheet may include a plurality of metal fibers randomly (or substantially randomly) distributed within the thickness of the sheet. In some implementations, the initial substrate sheet may be a reconstituted tobacco sheet as described above.

As noted above, the aerosol source member 700 of the depicted implementation also includes an overwrap substrate sheet 708 that extends around at least a portion of the substrate portion 702. In the depicted implementation, the overwrap substrate sheet 708 is similar to, or substantially the same as, the substrate sheet 300 described above with respect to FIG. 5. As such, the composition and construction of the overwrap substrate sheet 708 may be similar to, or substantially the same as, that described above with respect to the substrate sheet 300. For example, in the depicted implementation, the overwrap substrate sheet 708 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a polymeric fiber material coated with a metal material, or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a series of bands 712, separated by a series of spaces 714 in between, such that a segmented pattern is formed. Furthermore, in the depicted implementation, the series of bands 712 that comprise the heat conducting constituents are formed on the surface of the overwrap substrate sheet 708. Further reference is made to the discussion above with respect to various possible filler materials, aerosol forming materials, binder materials, and heat conducting constituents for use in the initial substrate sheet, and possible relative amounts of each.

As noted above, in some implementations, the overwrap substrate sheet 708 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet.

In various implementations, the segmented pattern may be created in a variety of ways, including, for example, by selective adhesion, metal printing, lamination, and/or stitching onto the formed overwrap substrate sheet 708. For example, in one implementation, the bands 712 may be created by selective powder coating of a heat conducting material onto a surface of the overwrap substrate sheet 708. In another implementation, the bands 712 may be created by electrostatically attracting the heat conducting material to a surface of the overwrap substrate sheet 708 and adhering the material in the segmented pattern to the overwrap substrate sheet 708. In another implementation, the bands 712 may be created using a masking template. In another implementation, the bands 712 may be created by printing a conductive metal material onto a surface of the overwrap substrate sheet 708 in the segmented pattern. In another implementation, the heat conducting material (for example, in the form of conductive yarns) may be stitched into the surface of the overwrap substrate sheet 708 such that the segmented pattern is formed. As noted above, in various implementations of an aerosol source member in which a substrate sheet is used as an overwrap substrate sheet, the resulting bands may have any orientation with respect to a longitudinal axis of the aerosol source member, including, for example, bands that are substantially transverse to a longitudinal axis of the aerosol source member, such as the depicted implementation. In other implementations, the bands may have any other angle with respect to a longitudinal axis of the aerosol source member, including, for example, substantially parallel to a longitudinal axis of the aerosol source member or angled with respect to a longitudinal axis of the source member.

As noted above, in various implementations, the mouth end portion 704 may comprise a variety of materials, which, in some implementations, may include a filter, as described above. Other materials that may be located in the mouth end portion, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. Reference is made to the above discussion of these components with respect to FIG. 6.

FIG. 15 is a schematic drawing of an aerosol source member 1300 according to an example implementation of the present disclosure. In the depicted implementation, the aerosol source member 1300 includes a substrate portion 1302, a mouth end portion 1304, and an overwrap substrate sheet 1308 extending around at least a portion of the substrate portion 1302. In various implementations, the overwrap substrate sheet 1308 may be separate from an optional exterior overwrap material, as discussed above. In various implementations, the substrate portion 1302 may comprise a collection of intermingled pieces 1306 that are cut from an initial substrate sheet. For example, in the depicted implementation, the collection of intermingled pieces 1306 are cut from an initial substrate sheet similar to, or substantially the same as, the substrate sheet 200 described above with respect to FIG. 4. As such, the composition and construction of the individual pieces 1306 may be the similar to, or substantially the same as, that described above with respect to the sheet 200. In particular, the intermingled pieces 1306 of the depicted implementation may start as an initial substrate sheet that comprises a mixture of a fibrous filler material, an aerosol forming material, a binder material, and a plurality of heat conducting constituents. Reference is made to the discussion above with respect to various possible filler materials, aerosol forming materials, binder materials, and heat conducting constituents for use in the initial substrate sheet and possible relative amounts of each. The initial substrate sheet may then be cut into a plurality of pieces (e.g., strips, sections, portions, etc.) and collected for use as the substrate portion 1302 of the aerosol source member 1300.

As described above, in some implementations, the initial substrate sheet may be constructed via a casting process, wherein the fibrous filler material, aerosol forming material, binder material, and plurality of heat conducting constituents may be blended together to form a slurry, which may be cast onto a surface (such as, for example, a moving belt). The cast slurry may then experience one or more drying and/or doctoring steps such that the result is a relatively consistent thickness initial sheet. In the case of the depicted implementation, the resulting initial sheet may include a plurality of metal fibers randomly (or substantially randomly) distributed within the thickness of the sheet. In some implementations, the initial substrate sheet may be a reconstituted tobacco sheet as described above.

As noted above, the aerosol source member 1300 of the depicted implementation also includes an overwrap substrate sheet 1308 that extends around at least a portion of the substrate portion 1302. In the depicted implementation, the overwrap substrate sheet 1308 is similar to, or substantially the same as, the substrate sheet 1200 described above with respect to FIG. 14. As such, the composition and construction of the overwrap substrate sheet 1308 may be similar to, or substantially the same as, that described above with respect to the substrate sheet 1200. For example, in the depicted implementation, the overwrap substrate sheet 1308 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a polymeric fiber material coated with a metal material, or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a metal mesh 1310 that has been laminated to a substrate sheet. Further reference is made to the discussion above with respect to various possible filler materials, aerosol forming materials, binder materials, and heat conducting constituents for use in the initial substrate sheet, and possible relative amounts of each.

As noted above, in some implementations, the overwrap substrate sheet 1308 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet. In other implementations, the initial substrate sheet may be a reconstituted tobacco sheet as described above.

As noted above, in various implementations of an aerosol source member in which a substrate sheet is used as an overwrap substrate sheet, the resulting pattern may have any orientation with respect to a longitudinal axis of the aerosol source member, including, for example, a pattern that is substantially aligned with a longitudinal axis of the aerosol source member, such as the depicted implementation. In other implementations, the pattern may have any other angle with respect to a longitudinal axis of the aerosol source member.

In various implementations, the mouth end portion 1304 may comprise a variety of materials, which, in some implementations, may include a filter, as described above. Other materials that may be located in the mouth end portion, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. Reference is made to the discussion of these components above with respect to FIG. 6.

FIG. 16 is a schematic drawing of an aerosol source member 1400 according to an example implementation of the present disclosure. In the depicted implementation, the aerosol source member 1400 includes a substrate portion 1402, a mouth end portion 1404, and an overwrap substrate sheet 1408 extending around at least a portion of the substrate portion 1402. In various implementations, the overwrap substrate sheet 1408 may be separate from an optional exterior overwrap material, as discussed above. In various implementations, the substrate portion 1402 may comprise a series of overlapping layers 1406 of an initial substrate sheet (e.g., a gathered web comprising an initial substrate sheet). For example, in the depicted implementation, the series of overlapping layers 1406 comprises layers of an initial substrate sheet similar to, or substantially the same as, the substrate sheet 200 described above with respect to FIG. 4. In another example implementation, the series of overlapping layers 1406 of an initial substrate sheet may be similar to, or substantially the same as, the substrate sheet 1200 of FIG. 14. As such, the composition and construction of the layers may be similar to, or substantially the same as, that described above with respect to the sheet 200 or sheet 1200. In particular, the overlapping layers of the depicted implementation may start as an initial substrate sheet that comprises a mixture of a fibrous filler material, an aerosol forming material, a binder material, and a plurality of heat conducting constituents. Reference is made to the discussions above with respect to various possible filler materials, aerosol forming materials, binder materials, and heat conducting constituents for use in the initial substrate sheet and possible relative amounts of each.

As described above, in some implementations, the initial substrate sheet may be constructed via a casting process, wherein the fibrous filler material, aerosol forming material, binder material, and plurality of heat conducting constituents may be blended together to form a slurry, which may be cast onto a surface (such as, for example, a moving belt). The cast slurry may then experience one or more drying and/or doctoring steps such that the result is a relatively consistent thickness initial sheet. In the case of the depicted implementation, the resulting initial sheet may include a plurality of metal fibers randomly (or substantially randomly) distributed within the thickness of the sheet. In other implementations, the initial substrate sheet may be a reconstituted tobacco sheet as described above.

As noted above, the aerosol source member 1400 of the depicted implementation also includes an overwrap substrate sheet 1408 that extends around at least a portion of the substrate portion 1402. In the depicted implementation, the overwrap substrate sheet 1408 is similar to, or substantially the same as, the substrate sheet 1200 described above with respect to FIG. 14. As such, the composition and construction of the overwrap substrate sheet 1408 may be similar to, or substantially the same as, that described above with respect to the substrate sheet 1200. For example, in the depicted implementation, the overwrap substrate sheet 1408 comprises a mixture of a fibrous filler material, an aerosol forming material, a binder material, and a plurality of heat conducting constituents. As noted above, in various implementations, the heat conducting constituents may be made of a metal material, a metal alloy material, a ceramic material, a polymeric fiber material coated with a metal material, or any combination thereof. In addition, in various implementations, the plurality of heat conducting constituents may take a granular form, a powder form, a fiber form, a mesh, a fiber cloth, or any combination thereof. In the depicted implementation, the heat conducting constituents comprise a metal mesh 1410 that has been laminated to a substrate sheet. The reference is made to the discussion above with respect to various possible filler materials, aerosol forming materials, binder materials, and heat conducting constituents for use in the initial substrate sheet, and possible relative amounts of each.

As noted above, in some implementations, the overwrap substrate sheet 1408 may be constructed via a casting process. For example, the fibrous filler material, aerosol forming material, and binder material may be blended together to form a slurry, which may be cast onto a surface (such as, for example, a moving belt). The cast slurry may then experience one or more drying and/or doctoring steps such that the result is a relatively consistent thickness sheet. In other implementations, the initial substrate sheet may be a reconstituted tobacco sheet as described above.

As noted above, in various implementations of an aerosol source member in which a substrate sheet is used as an overwrap substrate sheet, the resulting pattern may have any orientation with respect to a longitudinal axis of the aerosol source member, including, for example, a pattern that is substantially aligned with a longitudinal axis of the aerosol source member, such as the depicted implementation. In other implementations, the pattern may have any other angle with respect to a longitudinal axis of the aerosol source member.

As noted above, in various implementations, the mouth end portion 1404 may comprise a variety of materials, which, in some implementations, may include a filter, as described above. Other materials that may be located in the mouth end portion, either individually, or in any combination include, but are not limited to, tobacco blends, one or more flavorants, void spaces, and/or phase change materials. The mouth end portion 404 may also include a hollow tube structure. In various implementations, such a tube may be constructed from any of a variety of materials and may include one or more adhesives. Example materials include, but are not limited to, paper, paper layers, paperboard, plastic, cardboard, and/or composite materials. Reference is made to the above discussion of these components with respect to FIG. 6.

FIG. 10 illustrates various operations in a method 800 of manufacturing an aerosol generating substrate for use in an aerosol source member according to an example implementation of the present disclosure. In various implementations, the method 800 may comprise providing a fibrous filler material at operation 802, providing an aerosol forming material at operation 804, proving a binder material at operation 806, and providing a plurality of heat conducting constituents at operation 808. The method 800 may further comprise forming a substrate sheet using the fibrous filler material, aerosol forming material, binder material, and plurality of heat conducting constituents at operation 810. In various implementations, reference is made to the fibrous filler materials, aerosol forming materials, and binder materials, as well as substrate sheets, described above with respect to FIGS. 4-5.

FIG. 11 illustrates various operations in a method 900 of manufacturing an aerosol source member for use with an aerosol source delivery device according to an example implementation of the present disclosure. In various implementations, the method 900 may comprise forming an initial substrate sheet comprising a fibrous filler material, an aerosol delivery device, a binder material, and a plurality of heat conducting constituents at operation 902. The method 900 may further comprise cutting the initial substrate sheet into a plurality of pieces at operation 904, forming a collection of intermingled pieces from the plurality of pieces of the initial substrate sheet at operation 906, and forming a substrate portion using the collection of intermingled pieces at operation 908. In various implementations, reference is made to the fibrous filler materials, aerosol delivery materials, binder materials, and heat conducting constituents, as well substrate sheets, described above with respect to FIGS. 4-6 and 8.

FIG. 12 illustrates various operations in a method 1000 of manufacturing an aerosol source member for use with an aerosol source delivery device according to an example implementation of the present disclosure. In various implementations, the method 1000 may comprise forming an initial substrate sheet comprising a fibrous filler material, an aerosol delivery device, a binder material, and a plurality of heat conducting constituents at operation 1002. The method 1000 may further comprise overlapping a plurality of layers of the initial substrate sheet at operation 1004, and forming a substrate portion using the overlapping layers at operation 1006. In various implementations, reference is made to the fibrous filler materials, aerosol delivery materials, binder materials, and heat conducting constituents, as well as substrate sheets, described above with respect to FIGS. 4-5, 7 and 9.

FIG. 13 illustrates various operations in a method 1100 of manufacturing an aerosol source member for use with an aerosol source delivery device according to an example implementation of the present disclosure. In various implementations, the method 1100 may comprise forming a mixture comprising a fibrous filler material, an aerosol forming material, a binder material, and a plurality of heat conducting constituents at operation 1102. The method 1000 may further comprise extruding and spheronizing the mixture into a plurality of granules at operation 1104, and forming a collection of the granules at operation 1106. The method may further comprise forming a substrate portion using the collection of granules at operation 1108. It should be noted that in some implementations, the granules may be encapsulated spheres.

The present disclosure provides aerosol generating substrates and aerosol source members for use in aerosol delivery devices that use electrical energy to heat a heating member, which in turn heats a substrate material (preferably without combusting the substrate material to any significant degree) to form an inhalable substance such as an aerosol, the devices being sufficiently compact to be considered "hand-held" devices. In certain implementations, such devices may particularly be characterized as smoking articles. As used herein, the term is intended to mean a device or article that provides the taste and/or the sensation (e.g., hand-feel or mouth-feel) of smoking a cigarette, cigar, or pipe without the actual combustion of any component of the device. The term smoking device or article does not necessarily indicate that, in operation, the device produces smoke in the sense of the by-product of combustion or pyrolysis. Rather, smoking relates to the physical action of an individual in using the device—e.g., holding the device in a hand, drawing on one end of the device, and inhaling from the device. In further implementations, the inventive devices may be characterized as being vapor-producing devices, aerosolization devices, or pharmaceutical delivery devices. Thus, the devices may be arranged so as to provide one or more substances in an inhalable state.

As noted above, although an aerosol source member and a control body may be provided together as a complete smoking article or pharmaceutical delivery article generally, the components may be provided separately. For example, the present disclosure also encompasses a disposable unit for use with a reusable smoking article or a reusable pharmaceutical delivery article. In specific implementations, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various implementations of an aerosol source member (or cartridge) are described in U.S. Pat. No. 9,078,473 to Worm et al., which is incorporated herein by reference in its entirety.

In addition to the disposable unit, the disclosure further may be characterized as providing a separate control body for use in a reusable smoking article or a reusable pharmaceutical delivery article. In specific implementations, the control body may generally be a housing having a receiving end (which may include a receiving chamber with an open end) for receiving a heated end of a separately provided aerosol source member. The control body may further include an electrical energy source that provides power to an electrical heating member, which may be a component of the control body or may be included in aerosol source member to be used with the control unit. For example, in some implementations, the electrical energy source may power one or more heating assemblies that, in some implementations, may be a conductive heat source and/or an inductive heat source. In some implementations, one or more of the heating assemblies may be independent and/or separate from one or more other heating assemblies. Thus, in some implementations, there may be one or more conductive heating assemblies. In other implementations, there may be one or more inductive heating assemblies. In still other implementations, there may be one or more conductive heating assemblies and one or more inductive heating assemblies. In various implementations, the control body may also include further components, including an electrical power source (such as a battery), components for actuating current flow into the heating member, and components for regulating such current flow to maintain a desired temperature for a desired time and/or to cycle current flow or stop current flow when a desired temperature has been reached or the heating member has been heating for a desired length of time. In some implementations, the control unit further may comprise one or more pushbuttons associated with one or both of the components for actuating current flow into the heating member, and the components for regulating such current flow. The control body may also include one or more indicators, such as lights indicating the heater is heating and/or indicating the number of puffs remaining for an aerosol source member that is used with the control body.

Although some figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol source member comprising:
   a substrate comprising:
      a fibrous filler material;
      an aerosol forming material; and
      a plurality of heat conducting constituents; and
   an overwrap sheet enwrapping the substrate,
   wherein the overwrap sheet includes a plurality of heat conducting constituents comprising a series of bands formed on the surface of the overwrap sheet, and wherein the series of bands formed on the surface of the overwrap sheet are substantially perpendicular to a longitudinal axis of the aerosol source member.

2. The aerosol source member of claim 1, wherein the substrate comprises a substrate sheet comprising a mixture of the fibrous filler material, aerosol forming material, and plurality of heat conducting constituents.

3. The aerosol source member of claim 1, wherein the plurality of heat conducting constituents of the substrate sheet form a segmented pattern.

4. The aerosol source member of claim 3, wherein the segmented pattern comprises a series of bands comprising the plurality of heat conducting constituents.

5. The aerosol source member of claim 4, wherein the series of band are formed on the surface of the substrate sheet.

6. The aerosol source member of claim 1, wherein the substrate comprises a gathered web comprising overlapping layers of a substrate sheet comprising the fibrous filler material, aerosol forming material, and plurality of heat conducting constituents.

7. The aerosol source member of claim 6, wherein the plurality of heat conducting constituents of the substrate sheet form a segmented pattern.

8. The aerosol source member of claim 7, wherein the segmented pattern comprises a series of bands comprising the plurality of heat conducting constituents.

9. The aerosol source member of claim 8, wherein the series of band are formed on the surface of the substrate sheet.

10. The aerosol source member of claim 1, wherein the substrate comprises a collection of intermingled pieces of a substrate sheet comprising a mixture of the fibrous filler material, aerosol forming material, and plurality of heat conducting constituents.

11. The aerosol source member of claim 1, wherein the substrate comprises a plurality of granules comprising a mixture of the fibrous filler material, aerosol forming material, and plurality of heat conducting constituents.

12. The aerosol source member of claim 1, wherein a heated end of the aerosol source member includes at least a portion of the substrate, and wherein the aerosol source member further comprises a mouth end portion, opposite the heated end.

13. The aerosol source member of claim 12, wherein the mouth end portion includes a hollow tube structure.

14. The aerosol source member of claim 12, wherein the mouth end portion includes a filter.

15. The aerosol source member 12, wherein one or more components are located between the heated end and the mouth end portion.

* * * * *

UNITED STATES PATENT AND TRADEMARK OFFICE
CERTIFICATE OF CORRECTION

PATENT NO. : 11,882,867 B2
APPLICATION NO. : 17/244139
DATED : January 30, 2024
INVENTOR(S) : Andries Sebastian et al.

It is certified that error appears in the above-identified patent and that said Letters Patent is hereby corrected as shown below:

In the Claims

In Column 40, Line 36, in Claim 15, after "member" insert -- of claim --.

Signed and Sealed this
Thirtieth Day of April, 2024

*Katherine Kelly Vidal*

Katherine Kelly Vidal
*Director of the United States Patent and Trademark Office*